(12) United States Patent
Chait et al.

(10) Patent No.: US 7,244,396 B2
(45) Date of Patent: Jul. 17, 2007

(54) METHOD FOR PREPARATION OF MICROARRAYS FOR SCREENING OF CRYSTAL GROWTH CONDITIONS

(75) Inventors: Arnon Chait, Bay Village, OH (US); Lawrence DeLucas, Birmingham, AL (US); Brad Stoops, Bay Village, OH (US); Alexander Belgovskiy, Cleveland, OH (US)

(73) Assignee: UAB Research Foundation, Birmingham, AL (US)

( * ) Notice: Subject to any disclaimer, the term of this patent is extended or adjusted under 35 U.S.C. 154(b) by 466 days.

(21) Appl. No.: 10/278,771

(22) Filed: Oct. 23, 2002

(65) Prior Publication Data

US 2003/0232967 A1 Dec. 18, 2003

Related U.S. Application Data

(63) Continuation-in-part of application No. 10/208,576, filed on Jul. 30, 2002, which is a continuation-in-part of application No. 10/160,572, filed on May 30, 2002, and a continuation-in-part of application No. 10/160,906, filed on May 30, 2002, and a continuation-in-part of application No. 10/161,141, filed on May 30, 2002, and a continuation-in-part of application No. 09/947,655, filed on Sep. 6, 2001, which is a continuation-in-part of application No. 09/543,326, filed on Apr. 5, 2000, now abandoned.

(60) Provisional application No. 60/344,581, filed on Oct. 23, 2001, provisional application No. 60/328,958, filed on Oct. 12, 2001, provisional application No. 60/308,698, filed on Jul. 30, 2001, provisional application No. 60/128,018, filed on Apr. 6, 1999.

(51) Int. Cl.
*G01N 21/01* (2006.01)
*B01L 3/00* (2006.01)
*B01L 9/00* (2006.01)

(52) U.S. Cl. .................. 422/99; 422/100; 436/86; 436/807; 356/36; 356/244; 356/246; 359/368; 359/372; 359/373; 382/128

(58) Field of Classification Search ............... 356/36, 356/244, 246; 359/368, 372, 373; 382/128; 422/99, 100; 436/86, 807
See application file for complete search history.

(56) References Cited

U.S. PATENT DOCUMENTS 3,570,515 A 3/1971 Kinner (Continued)

FOREIGN PATENT DOCUMENTS

AU 779792 6/2005

(Continued)

OTHER PUBLICATIONS

Ahn et al., Fluid Micropumps Based on Rotary Magnetic Actuators, Proceedings of 1995 IEEE Micro Electro Mechanical Systems Workshop (MEMS '95), held in Amsterdam, Netherlands on Jan. 29-Feb. 2, 1995, pp. 408-412 (1995).

(Continued)

*Primary Examiner*—Monique T. Cole
(74) *Attorney, Agent, or Firm*—Bingham McCutchen LLP

(57) ABSTRACT

A method of screening solution conditions suitable for the crystallization of macromolecules with a picogram to a microgram of protein using picoliter or nanoliter volumes is provided. A preferred method comprises preparing a plurality of recipe solutions in milliliter volumes, aspirating protein and recipe solutions, respectively, from a plurality of wells, and dispensing the protein and recipe solutions into a plurality of wells, covering the combined protein and recipe solutions with oil, and maintaining the solution wells until crystallization or precipitation occur therein.

13 Claims, 11 Drawing Sheets

U.S. PATENT DOCUMENTS

| | | | |
|---|---|---|---|
| 3,747,628 A | 7/1973 | Holster et al. |
| 4,046,159 A | 9/1977 | Pegourie |
| 4,119,368 A | 10/1978 | Yamazaki |
| 4,153,855 A | 5/1979 | Feingold |
| 4,245,673 A | 1/1981 | Bouteille et al. |
| 4,263,010 A | 4/1981 | Randolph |
| 4,434,704 A | 3/1984 | Surjaatmadja |
| 4,517,048 A | 5/1985 | Shlichta |
| 4,668,584 A | 5/1987 | Uzgiris et al. |
| 4,755,363 A | 7/1988 | Fujita et al. |
| 4,833,233 A | 5/1989 | Carter |
| 4,886,646 A | 12/1989 | Carter et al. |
| 4,898,582 A | 2/1990 | Faste |
| 4,900,147 A | 2/1990 | Bowley et al. |
| 4,909,933 A | 3/1990 | Carter et al. |
| 4,919,899 A | 4/1990 | Herrmann et al. |
| 4,948,564 A | 8/1990 | Lyman et al. |
| 5,009,861 A | 4/1991 | Plaas-Link |
| 5,013,531 A | 5/1991 | Snyder et al. |
| 5,076,698 A | 12/1991 | Smith et al. |
| 5,078,975 A | 1/1992 | Rhodes et al. |
| 5,085,562 A | 2/1992 | Van Lintel |
| 5,088,515 A | 2/1992 | Kamen |
| 5,096,388 A | 3/1992 | Weinberg |
| 5,096,676 A | 3/1992 | McPherson et al. |
| 5,106,592 A | 4/1992 | Stapelmann et al. |
| 5,124,935 A | 6/1992 | Wallner et al. |
| 5,126,115 A | 6/1992 | Fujita et al. |
| 5,130,105 A | 7/1992 | Carter et al. |
| 5,164,558 A | 11/1992 | Huff et al. |
| 5,171,132 A | 12/1992 | Miyazaki et al. |
| 5,193,685 A | 3/1993 | Trevithick |
| 5,221,410 A | 6/1993 | Kushner et al. |
| 5,224,843 A | 7/1993 | Van Lintel |
| 5,256,241 A | 10/1993 | Noever |
| 5,259,737 A | 11/1993 | Kamisuki et al. |
| 5,265,327 A | 11/1993 | Faris et al. |
| 5,290,240 A | 3/1994 | Horres, Jr. |
| 5,336,062 A | 8/1994 | Richter |
| 5,346,372 A | 9/1994 | Naruse et al. |
| 5,375,979 A | 12/1994 | Trah |
| 5,376,252 A | 12/1994 | Ekstrom et al. |
| 5,400,741 A | 3/1995 | DeTitta et al. |
| 5,419,278 A | 5/1995 | Carter |
| 5,423,287 A | 6/1995 | Usami et al. |
| 5,529,465 A | 6/1996 | Zengerle et al. |
| 5,544,254 A | 8/1996 | Hartley et al. |
| 5,581,476 A | 12/1996 | Osslund |
| 5,593,130 A | 1/1997 | Hansson et al. |
| 5,637,469 A | 6/1997 | Wilding et al. |
| 5,641,681 A | 6/1997 | Carter |
| 5,642,015 A | 6/1997 | Whitehead et al. |
| 5,643,540 A | 7/1997 | Carter et al. |
| 5,659,171 A | 8/1997 | Young et al. |
| 5,660,370 A | 8/1997 | Webster |
| 5,681,024 A | 10/1997 | Lisec et al. |
| 5,705,018 A | 1/1998 | Hartley |
| 5,728,559 A | 3/1998 | Nilsson et al. |
| 5,759,014 A | 6/1998 | Van Lintel |
| 5,775,371 A | 7/1998 | Pan et al. |
| 5,790,421 A | 8/1998 | Osslund |
| 5,836,750 A | 11/1998 | Cabuz |
| 5,855,753 A | 1/1999 | Trau et al. |
| 5,869,604 A | 2/1999 | Rousseau et al. |
| 5,872,010 A | 2/1999 | Karger et al. |
| 5,873,394 A | 2/1999 | Meltzer |
| 5,875,817 A | 3/1999 | Carter |
| 5,876,187 A | 3/1999 | Afromowitz et al. |
| 5,885,470 A | 3/1999 | Parce et al. |
| 5,932,799 A | 8/1999 | Moles |
| 5,942,443 A | 8/1999 | Parce et al. |
| 5,958,694 A | 9/1999 | Nikiforov |
| 5,961,934 A | 10/1999 | Arnowitz et al. |
| 5,973,779 A | 10/1999 | Ansari et al. |
| 5,985,356 A | 11/1999 | Schultz et al. |
| 5,997,636 A | 12/1999 | Gamarnik et al. |
| 6,007,309 A | 12/1999 | Hartley |
| 6,031,082 A | 2/2000 | Nielsson et al. |
| 6,036,920 A | 3/2000 | Pantoliano et al. |
| 6,039,804 A | 3/2000 | Kim et al. |
| 6,043,080 A | 3/2000 | Lipshutz et al. |
| 6,057,159 A | 5/2000 | Lepre |
| 6,069,934 A | 5/2000 | Verman et al. |
| 6,110,986 A | 8/2000 | Nozawa et al. |
| 6,155,282 A | 12/2000 | Zachary et al. |
| 6,174,675 B1 | 1/2001 | Chow et al. |
| 6,268,158 B1 | 7/2001 | Pantoliano et al. |
| 6,291,192 B1 | 9/2001 | Pantoliano et al. |
| 6,296,673 B1 | 10/2001 | Santarsiero et al. |
| 6,296,811 B1 | 10/2001 | Sasaki |
| 6,297,021 B1 | 10/2001 | Nienaber et al. |
| 6,303,322 B1 | 10/2001 | Pantoliano et al. |
| 6,387,273 B1 | 5/2002 | Abedi |
| 6,402,837 B1 | 6/2002 | Shtrahman et al. |
| 6,404,849 B1 | 6/2002 | Olson et al. |
| 6,406,903 B2 | 6/2002 | Bray et al. |
| 6,409,832 B2 | 6/2002 | Weigl et al. |
| 6,413,778 B1 | 7/2002 | Carpenter et al. |
| 6,417,007 B1 | 7/2002 | Gittleman et al. |
| 6,423,536 B1 | 7/2002 | Jovanovich et al. |
| 6,468,346 B2 | 10/2002 | Arnowitz et al. |
| 6,630,006 B2 | 10/2003 | Santarsiero et al. |
| 2001/0016191 A1 | 8/2001 | Osslund |
| 2001/0016314 A1 | 8/2001 | Anderson et al. |
| 2001/0019845 A1 | 9/2001 | Blenert et al. |
| 2001/0027745 A1 | 10/2001 | Weigl et al. |
| 2001/0032582 A1 | 10/2001 | DeTitta et al. |
| 2001/0055669 A1 | 12/2001 | Schultz et al. |
| 2001/0055775 A1 | 12/2001 | Schultz et al. |
| 2002/0022250 A1 | 2/2002 | Hendrickson et al. |
| 2002/0029814 A1 | 3/2002 | Unger et al. |
| 2002/0048610 A1 | 4/2002 | Cima et al. |
| 2002/0054663 A1 | 5/2002 | Olson et al. |
| 2002/0062783 A1 | 5/2002 | Bray |
| 2002/0064485 A1 | 5/2002 | Delucas et al. |
| 2002/0067800 A1 | 6/2002 | Newman et al. |
| 2002/0164812 A1 | 11/2002 | DeLucas |
| 2003/0022383 A1 | 1/2003 | DeLucas |
| 2003/0022384 A1 | 1/2003 | DeLucas |
| 2003/0027348 A1 | 2/2003 | DeLucas |
| 2003/0096421 A1 | 5/2003 | DeLucas et al. |
| 2003/0180960 A1 | 9/2003 | Consenza et al. |

FOREIGN PATENT DOCUMENTS

| | | |
|---|---|---|
| EP | 0 553539 A1 | 8/1993 |
| EP | 592 094 | 4/1994 |
| EP | 703 384 | 3/1996 |
| EP | 706 004 | 4/1996 |
| EP | 779 436 | 6/1997 |
| EP | 829 360 | 3/1998 |
| EP | 845 603 | 8/1998 |
| EP | 999 055 | 10/2000 |
| GB | 2 155 152 | 9/1985 |
| GB | 2 308 460 | 6/1997 |
| JP | 02001013054 A | 1/2001 |
| NZ | 514732 | 1/2004 |
| WO | WO 98/07069 | 2/1998 |
| WO | WO 99/00655 | 1/1999 |
| WO | WO 99/04361 | 1/1999 |
| WO | WO 99/17093 | 4/1999 |
| WO | WO 99/52633 | 10/1999 |

| | | |
|---|---|---|
| WO | WO 00/00678 | 1/2000 |
| WO | WO 00/43748 | 7/2000 |
| WO | WO 00/60345 A1 | 10/2000 |
| WO | WO 01/09595 | 2/2001 |
| WO | WO 01/26797 A2 | 4/2001 |
| WO | WO 01/92293 A2 | 12/2001 |
| WO | WO 03/012430 | 2/2003 |

OTHER PUBLICATIONS

Andersson et al., "Consecutive Microcontact Printing—Ligands for Asymmetric Catalysis in Silicon Channel," Sensors and Actuators, B, 3997, 2001, pp. 1-7.

Bellec et al., "In situ time-resolved FTIR spectroelectrochemistry: study of the reduction of TCNQ," Eletrochem. Commun. 3:483-488 (2001).

Benard et al., "A Titanium-Nickel Shape-Memory Alloy Actuated Micropump," Proceedings of Transducers '97, 1997 International Conference on Solid-State and Actuators, held in Chicago, Illinois, Jun. 16-19, 1997, 1:361-364 (1997).

Bordin et al., "Identification and quantification of major bovine milk proteins by liquid chromatography," J. Chromatograph A 928:63-76 (2001).

Boussad et al., "High-Resolution Multiwavelength Surface Plasmon Resonance Spectroscopy for Probing Conformational and Electronic Changes in Redox Proteins," Anal. Chem. 72:222-226 (2000).

Brechtel et al., "Control of the Electroosmotic Flow by Metal-salt-containing Buffers," J Chromatography A, 716:-97-105 (1995).

Brochure: "JASCO—Pioneering in modern protein science: UV/Vis, FTIR, Raman, CD," Unverified date.

Bryzek et al., "Micromachines on the March," 8045 IEEE Spectrum, 31(5):20-31 (1994. XP 000456261.

Buchaillot et al., "Silicon Nitride ThinFilms Young's Modulus Determination by an Optical Non-Destructive Method," Jpn. J. Appl. Phys., 36 Pt. 2(6B):L794-:L797 (1997).

Carter et al., "Protein Crystallization Using Incomplete Factorial Experiments," Journal of Biological Chemistry, 1979, pp. 12219-12223, vol. 254, No. 23.

Carter et al., "Statistical Design of Experiments for Protein Crystal Growth and the Use of a Precrystallization Assay," Journal of Crystal Growth 90, 1998, pp. 60-73.

Chappell et al., "Quantitative analysis of chromium(V) by EPR spectroscopy," Talanta 46:23-38 (1998).

Chiu et al., "Patterned Deposition of Cells and Proteins Onto Surfaces by Using Three-Dimensional Microfluidic Systems," PNAS, 97(6):2408-2413 (2000).

Chou et al., "A Microfabricated Device for Sizing and Sorting DNA Molecules," PNAS, 96:11-13 (1999).

Clarke and Kane, "Optical detection of membrane diopole potential: avoidance of fluidity and dye-induced effects," Biochimica Biophysica Acta 1323(2):223-239 (Jan. 31, 1997).

Codina et al., "Combined use of ESI-MS and UV diode-array detection for localization of disulfide bonds in proteins: application to an $\alpha$-L-fucosidase of pea," J. Peptide Res. 57:473-482 (2001).

D'Alessio et al., "Absorption spectroscopy of toluene pyrolysis," Optics and Lasers in Engineering 37:495-508 (2002).

Delamarche et al., "Patterned Delivery of Immunoglobulins to Surfaces Using Microfluidic Networks," Science, 276:779-781 (1997).

Ducruix et al., "Methods of Crystallization in Crystallization of Nucleic Acids and Proteins—A Practical Approach," IRL Press, Oxford, 1992.

Duffy et al., "Patterning Electroluminescence Materials with Feature Sizes as Small as 5 μm Using Elastomeric Membranes as Masks for Dry Lift-Off," Adv. Mater. 11(7):546-552 (1999), XP-000849014.

Duffy et al., "Rapid Prototying of Microfluidic Switches in Poly(dimethyl siloxane) and Their Actuation by Electro-Osmotic Flow," J. Micromech. Microeng., 9:211-217 (1999).

Duffy et al., "Rapid Prototyping of Microfluidic Systems in Poly(dimethylsiloxane)," Analytical Chemistry, 70(23):4974-4984 (1998).

Effenhauser et al., "Integrated Capillary Electrophoresis on Flexible Silicone Microdevices: Analysis of DNA Restriction Fragments and Detection of Single DNA Molecules and Microchips," Anal. Chem. 69(17):3451-3457 (1997).

Effenhauser et al., "Integrated Chip-Based Capillary Electrophoresis," Electrophoresis, 18:2203-2213 (1997).

Fahrenburg et al., "A Microvalve System Fabricated by Thermoplastic Molding," J. Micromech. Microeng., 5:169-171 (1995).

Feher and Kam, "Diffraction Methods for Biological Macromolecules," eds. Wyckoff and Hirs, Methods in Enzymology, eds. in chief Colonick and Kapler, 19785, Academic Press, Orlando, 77-113.

Fu et al., "A Microfabricated Fluorescence-Activated Cell Sorter," Nature Biotechnology, 17:1109-111 (1999).

Gass et al., "Integrated Flow-Regulated Silicon Micropump," Sensors and Actuators A, 4335-4338 (1994).

Gerlach, T., "Pumping Gases by a Silicon Micro Pump with Dynamic Passive Valves," Proceedings of Transducers '97, 1997 International Conference on Solid-State Sensors and Actuators held in Chicago, Illinois, Jun. 16-19, 1997, 1:357-360 (1997).

Goll et al., "Microvalves with Bilstable Buckled Polymer Diaphragms," J. Micromech. Microeng., 6:77-79 (1996).

Graveson et al., "Microfluidics—A Review," J. Micromech. Microeng., 3:168-182 (1993).

Grube et al., "IR-spectroscopic studies of *Zymomonas mobilis* and leval precipitate," Vibrat. Spectro. 28:277-254 (2000).

Harrison et al., "Micromachining a Miniaturized Capillary Electrophoresis-Based Chemical Analysis System on a Chip," Science, 261:895-897, (1993).

Hautala et al., "Measurement of aquatic humus content by spectroscopic analyses," Wat. Res. 34(1):246-254 (2000).

Hayakawa et al., "Protein determination by high-performance gel-permeation chromatography: applications to human pancreatic juice, human bile and tissue homogenate," J. Chromatography B 754:65-76 (2001).

Hayakawa et al., "Serum protein determination by high-performance gelpermeation chromatography," J. Chromatography B696:19-23 (1997).

Heremans and Heremans, "Pressure Effects on the Raman Spectrum of Proteins: Stability of the Salt Bridge in Trysin and Elastase," J. Mol. Struct. 214:305-314 (1989).

Holler et al., "Synthesis and spectroscopic characterization of 2-(2'-hydroxyphenyl)benzazole isothiocyanates as new fluorescent probes for proteins," J. Photochem. Photobiol. A: Chem. 149:217-225 (2002).

Hornbeck et al., "Bistable Deformable Mirror Device," Spatial Light Modulators and Applications 1988 Technical Digest Series,, vol. 8, Postconference Edition, Summaries of papers presented at the Spatial Light Modulators and Applications Topical Meeting, Jun. 15-17, 1988, Optical Society of America, pp. 107-110.

Hosokawa et al., "Handling of Picoliter Liquid Samples in a Poly(dimethylsiloxane)-Based Microfluidic Device," Anal. Chem. 71(20):4781-4785 (1999).

Ikuta et al., "Three Dimensional Micro Integrated Fluid Systems (MIFS) Fabricated By Stereo Lithography," IEEE Kyushu Institute of Technology, pp. 1-6 (1994).

Jacobson et al., "High-Speed Separations on a Microchip," Anal. Chem., 6(7):1114-1118 (1994).

Jacobson et al., "Microfluidic Devices for Electrokinetically Driven Parallel and Serial Mixing," Anal. Chem., 71(20):4455-4459 (1999).

Jancura et al., "Surface-enhanced resonance Raman spectroscopy of hypocrellin A: an effect of excitation wavelength and pH," Spectrochimica Acta part A 54:1519-1526 (1998).

Jaramillo et al., "Crystallization and Crystallography inside X-ray capillaries," J. Appl. Cryst. (2001). 34, pp. 365-370.

Jerman H., "Electrically-Activated Normally-Closed Diaphragm Valves," Proceedings of Transducers, '91, 1991 International Conference on Solid-State Sensors and Actuators, pp. 1045-1048 (1991).

Jung et al., "Chemical and Physical Interactions at Metal/Self-Assembled Organic Monolayer Interfaces," Critical Reviews in Solid State and Material Sciences, 19(1):2-10 (1994).

Kamholz et al., "Quantitative Analysis of Molecular Interaction in a Microfluidic Channel: The T-Sensor," Analytical Chemistry, vol. 71, No. 23, Dec. 1, 1999, pp. 5340-5347.

Kenis et al., "Microfabrication Inside Capillaries Using Multiphase Laminar Flow Patterning," Science, 2985:83-85 (1999).

Kopp et al., "Chemical Amplification: Continuous-Flow PCR on a Chip," Science, 280:1046-1048 (1998).

Kudryavtsev et al., "Polarized Raman Spectroscopic Studies of Tetragonal Lysozyme Single Crystals," Acta Cryst. D54:1216-1229 (1998).

Kudryavtsev et al., "The effect of ordering of internal water in thaumatin and lysozyme crystals as revealed by Raman method," J. Crystal Growth 219(1-2):102-114 (Oct. 1, 2000).

Kuhn et al., "Silicon Charge Electrode Array for Ink Jet Printing," IEEE Transactions on Electron Devices, ED-25(10):1257-1260 (1978).

Lin et al., Convective-diffusive transport in protein crystal growth, Journal of Crystal Growth, 151 (1985), pp. 153-162.

Lin et al., "Free-Space Micromachined Optical Switches for Optical Networking," IEEE J. Selected Topics in Quantum Electronics, 5(1):4-9 (1999).

Lis, "Luminescence spectroscopy of lanthanide(III) ions in solution," J. Alloys Comp. 341:45-50 (2002).

Lötters et al., "The Mechanical Properties of the Rubber Elastic Polymer Polydimethylsiloxane for Sensor Applications," J. Micromech. Microeng. 7:145-147 (1997).

Lucy et al., "Characterization of the Cationic Surfactant Induced Reversal of Electroosmotic Flow in Capillary Electrrophoresis," Anal. Chem. 68:300-305 (1996).

Luft et al., "Kinetic Aspects of Macromolecular Crystallization," Methods in Enzymology, 1997, pp. 110-130, vol. 276.

Luft et al., "Microbatch Macromolecular Crystallization in Micropipettes," Journal of Crystal Growth, 196 (1999), pp. 450-455.

Mach et al., "Detection of Proteins and PHenol in DAN Samples with Second-Derivative Absorption Spectroscopy," Anal. Biochem. 200:20-26 (1992).

Maluf et al., "An Introduction to Microelectromechanical Systems Engineering," Artech House Publishers, Boston London pp. 42-45.

Markx et al., "Applications of Dielectrophoresis in Biotechnology," Tibtech., 15:426-432 (1997).

McPherson et al., "Crystallization of Proteins by Variations of pH of Temperature," Methods Enzymol., 1985, 114: pp. 120-125.

McPherson, "Crystallization of Macromolecules: General Principles," Methods Enzymol., 1985, pp. 114, 112.

Menezes, et al. "Identification and Entity Authentication," Handbook of Aplied Cryptography, CRC Press Chapter 10 pp. 405-417 (1996) (XP002258705).

Miller et al., "A Comparison between Protein Crystals Growth with Vapor Diffusion Methods in Microgravity and Protein Crystals using a Gel Liquid-liquid diffusion Ground-Based Method," *Journal of Crystal Growth*, 32 (1992), pp. 306-309.

Mino et al., "Hydrogen Bonding of Sulfur Ligands in Blue Copper and Iron-Sulfur Proteins: Detection by Resonance Raman Spectroscopy," Biochem. 26:8059-8065 (1987).

Miteva et al., "Spectrophotometric titration of ionisable groups in proteins: a theoretical study," Spectrochimica Acta Part A 56:2033-2041 (2000).

Moffat and Ren, "Synchrotron radiation applications to macromolecular crystallography," Curr. Opin. Struct. Biol. 7:689-696 (1997).

Moffatt et al., "Approaches towards the quantitative analysis of peptides and proteins by reversed-phase high-performance liquid chromatography in the absence of a pure reference sample," J. Chromatography A 891:235-242 (2000).

Muller et al., "Surface-Micromachined Microoptical Elements and Systems," Proceedings of IEEE, 86(8):1705-1720 (1998).

Nerad et al., "Ground-Based Experiments on the Minimization of Convention During the Growth of Crystals From Solution," Journal of Crystal Growth, 1986, pp. 591-608, vol. 75.

Olsson et al., "Simulation Studies of Diffuser and Nozzle Elements for Valve-less Micropumps," Proceedings of Transducers '97, 1997 International Conference on Solid-State Sensors and Actuators, held in Chicago, Illinois, Jun. 16-19, 1997, 2:1039-1042 (1997).

Pandher et al., "Spectroscopy, persistent hole burning, and holographic applications of naphtophthalocyanine/haloanthracene systems," J. Lumin. 98:207-212 (2002).

Phillips, "Crystallization in Capillary Tubes," Methods Enzymol. 1985; 114: pp. 128-131.

Platoff, Jr. et al., "Serial Capillary Gas Chromatography/Fourier Transform Infrared Spectrometry/Mass Spectrometry (GC/IR/MS): Qualitative and Quantitative Analysis of Amphetamine, Methamphetamine and Related Analogues in Human Urine," J. Anal. Toxicol. 16:389-397 (Nov./Dec. 1992).

Qin et al., "Photolithography with Transparent Reflective Photomasks," J. Vac. Sci. Technology, 16(1):98-103 (1998).

Qin et al., "Elastomeric Light Valves""," Adv. Mater., 9(5):407-410 (1997). XP-000683891.

Quake et al., "From Micro- to Nanofabrication with Soft Materials," Science, vol. 2990, pp. 1536-1540 (2000).

Rapp R., "LIGA micropump for gases and liquids," Sensors and Actuators A, 40:57-61 (1994).

Roylance et al., "A Batch-Fabricated Silicon Accelerometer," IEEE Transactions on Electron Devices, ED-26(12):1911-1917 (1979).

Rückert et al., "Characterization of protein mixtures by ion-exchange chromatography coupled on-line to nuclear magnetic resonance spectroscopy," J. Chromatography A 840:131-135 (1999).

Ruiz et al., "Agarose as Crystallization Media for Proteins 1: Transport Processes," Journal of Crystal Growth, 2001, pp. 165-172, vol. 232.

Ruiz et al., "Investigations on Protein Crystal Growth by the Gel Acupuncture Method," Acta Crystallographica, 1994, pp. 484-490, Section D.

Salemme, "A Free Interface Diffusion Technique for the Crystallization of Proteins for X-Ray Crystallography," Archives of Biochemistry and Biophysics, 1972, pp. 533-539, vol. 151.

Sane et al., "A Holistic Approach to Protein Secondary Structure Characterization Using Amide I Band Raman Spectroscopy," Anal. Biochem. 269:255-272 (1999).

Sanjoh et al., "Spatiotemporal Protein Crystal Growth Studies using Microfluidic Silicon Devices," Journal of Crystal Growth, 196 (1999), pp. 691-702.

Šašić and Ozaki, "Short-Wave Near-Infrared Spectroscopy of Biological Fluids. 1. Quantitative Analysis of Fat, Protein, and Lactose in Raw Milk by Partial Least-Squares Regression and Band Assignment," Anal. Chem. 73:64-71 (2001).

Schasfoort et al., "Field-Effect Flow Control for Microfabricated Fluidic Networks," Science, 266:942-945 (1999).

Schueller et al., "Fabrication of Glassy Carbon Microstructures by Soft Lithography," Sensors and Actuators, 72(2):125-139 (1999).

Shoji et al., "Smallest Dead Volume Microvalves for Integrated Chemical Analyzing Systems," Proceedings of Transducers '91, 1991, International Conference on Solid-State Sensors and Actuators, pp. 1052-1055 (1991).

Shoji, S., "Fluids for Sensor Systems," Topics in Current Chemistry, 194:162-188 Springer Verlag Berlin Heidelberg (1998).

Smits, J.G., "Piezoelectric Micropump with Three Valves Working Peristaltically," Sensors and Actuators, A21-A23:203-206 (1990).

Sohn et al., "Capacitance Cytometry: Measuring Biological Cells One By One," PNAS, 97(20):10687-10690 (2000).

Thomas et al., "Distribution coefficients of Protein Impurities in Ferritin and Lysozyme Crystals Self-Purification in Microgravity," Journal of Crystal Growth 211 (2000), pp. 149-156.

Thomas, Jr., "Raman Spectroscopy of Protein and Nucleic Acid Assemblies," Ann. Rev. Biophys. Biomol. Struct. 28:1-27 (1999).

Thompson et al., "Remote microwave wavelength spectrometry using an infrared fibre optic telecommunication network," Anal. Chimica Acta 463:1-4 (2002).

Tufte et al., "Silicon Diffused-Element Piezoresistive Diaphragms," J. Appl. Phys., 33(11):3322-3327 (1982).

Unger et al., "Monolithic Microfabricated Valves and Pumps by Multilayer Soft Lithography," Science, vol. 288, pp. 113-118 (2000).

Van der Pol et al., "A Thermo-Pneumatic Actuation Principle for Microminiature Pump and Other Micromechanical Devices," Sensors and Actuators, 17:139-143(1989).

Van der Pol et al., "Micro Liquid Handling Devices—A Review," Micro Systems Technologies, 90:799-805 (1990).

Van Iersel et al., "Determination of Absorptoin Coefficients of Purified Proteins by Conventional Ultraviolet Spectrophotometry and Chromatography Combined with ultiwavelength Detection," Anal. Biochem. 151:196-204 (1985).

Vieder et al., "A Pneumatically Actuated Micro Valve with a Silicone Rubber Membrane for Integration with Fluid-Handling Systems," Proceedings of Transducers '95, the 8th International Conference on Solid-State Sensors and Actuators and Eurosensors IX, held in Stockholm, Sweden on Jun. 25-29, 1995,, 2:284-286 (1995).

Wagner et al., "Protein mapping by two-dimensional high performance liquid chromatography," J. Chromatography A 893:293-305 (2000).

Ward et al., "Automatic Preparation of Protein Crystals Using Laboratory Robotics and Automated Visual Inspection," Journal of Crystal Growth 90 (1988), pp. 325-339.

Washizu et al., "Molecular Dielectrophoresis and Biopolymers," IEEE Transactions on Industry Applications, 30(4):835-843 (1994).

WEBSITE: "High-Resolution UV Spectroscopy," http://physics.nist.gov/Divisions/Div844/facilities/uvs/uvs.html unverified print date of Jul. 1, 2002.

WEBSITE: "Olympus Microscopes BX40 and BX50," http://www.imebinc.com/pages/BX4050.html (Sep. 30, 2000).

WEBSITE: Garcia-Ruiz, J.M., "The role of gravity in protein crystallization: is there an effect of gravity on the crystallization process," printed from http://lec.ugr.es/esart/Role_of_gravity/Role.html on Apr. 11, 2002 (3 pages).

Wröbel and Boguta, "Study of the influence of substituents on spectroscopic and photoelectric properties of zinc phthalocyanines," J. Photchem. Photobiol. A: Chem 6045:1-10 (2002).

Wu et al., "MEMS Flow Sensors for Nano-Fluidic Applications," Sensors and Actuators A 89, 2001 pp. 152-158.

Xia et al., "Micromolding in Capillaries: Applications in Material Science," J. American Chemical society, 118:5722-5731 (1996).

Xia et al., "Micromolding of Polymers in Capillaries: Applications in Microfabrication," Chemistry of Materials, 8(7):1558-1587 (1996).

Xia et al., "Soft Lithography," Angew. Chem. Int. Ed., 37:551-575 (1998).

XP-002149046, Ullman's Encyclopedia of Industrial Chemistry, Sixth Edition, 1999 Electronic Release, 6 pages.

Yang et al., "A MEMS Thermopneumatic Silicone Membrane Valve," Proceedings of the IEEE 10th Annual Workshop of Micro Electro Mechanical Systems Workshop (MEMS '97), held Jan. 26-30, 1997 in Nagoya, Japan, pp. 114-118 (1997).

Yang et al., "A Mems Thermopneumatic Silicone Membrane Valve, Proceedings of IEEE 10th Annual International Workshop on MicroElectro Mechanical Systems," Sensors and Actuators, A64(1):101-108 (1998).

Yazdi et al., "Micromachined Intertial Sensors," Proceedings of IEEE, 86(8):1640-1659 (1998).

Young et al., "Contoured Elastic-Membrane Microvalves for Microfluidic Network Integration," J. Biomechanical Engineering, 121:2-6 (1999).

Zengerle et al., "A Micro Membrane Pump with Electrostatic Actuation," 1992 IEEE Conf. on Micro Electro Mechanical Systems, held Feb. 4-7, 1992 in Travemunde Germany, pp. 19-24.

Zengerle et al., "Performance Simulation of Microminiaturized Membrane Pumps," from 7th International Conference on Solid-State Sensors and Actuators Jun. 7-10, 1993 in Yokohama, Japan, pp. 108-109.

"BMST Pervasive Technologies—Concept Paper, BMST Initiative Thrust Area: Emerging of Breakthrough Process Technologies—Definition of the Thrust Area—NACFAM," printed from http://www.nacfam.org/bmst/bmstemergingtechnologies.html on Feb. 26, 2002 (5 pages).

"Hampton Research—Solutions for Crystal Growth," printed from http://www.hamptonresearch.com on Feb. 22, 2001 (2 pages).

"High throughput protein crystallization—EMBL Practical Course on Protein Expression, Purification and Crystallization—Aug. 14-20, 2000 EMBL Outstation Hamburg, Germany," printed from http://www.structure.llnl.gov/Xray/tutorial/High_Throughput_EMBL_full.html on Apr. 12, 2002 (10 pages).

"High-Throughput Structure Determination in an Informatics Environment," (2001) printed from http://www.accelrys.com/wbezine on Aug. 1, 2002 (4 pages).

"Meeting Summaries," printed from http://www-nmr.cabm.rutgers.edu/labdocuments/mtgsummaries/mtgsummaries.html on Apr. 12, 2002 (32 pages).

"Minutes May 1-2, 2001—Biological and Environmental Research Advisory Committee (BERAC)," printed from http://www.er.doe.gov/production/ober/berac/5-01mins.html on Apr. 12, 2002 (10 pages).

"NIGMS—Advisory Council Meeting Minutes, May 1998—Minutes of the National Advisory General Medical Sciences Council—May 14-15, 1998," printed from http://www.nigms.nih.gov/about_nigms/council_may98.html on Apr. 12, 2002 (10 pages) (site last updated Jul. 17, 1998).

"NIGMS- NIGMS Structural Genomics Targets Workshop Feb. 11-12, 1999" printed from http://www.nigms.nih.gov/news/meetings/structural_genomics_targets.html on Apr. 12, 2002 (18 pages).

"NIGMS Protein Structure Initative Meeting Summary Apr. 24, 1998," printed from http://www.nigms.nih.gov/news/reports/protein_structure.html on Apr. 12, 2002 (12 pages) (site last updated Jun. 2, 1998).

"RAMC 1999—Round Table Notes," particularly regarding Robotics (starting at bottom of 1st page), printed from www.hamptonresearch.com/stuff/RAMC99RTN.html._om_08/21/2002 (7 pages).

Abbott, A. "Structures by numbers," Nautre 408:130-132 (Nov. 9, 2000).

Abola et al., "Automation of X-ray crystallography," Nat. Struc. Biol. (Structural Genomics Supplement:973-977 (Nov. 2000)Mochalkin et al., "High-Throughput Structure Determination in an Informatics Environment," (2001) print from http://www.accelrys.com webzine on Aug. 1, 2002 (4 pages).

Adersen, G.R. et al., "A Spreadsheet Approach to Automated Protein Crystallization," J. Appl. Cryst. 29:236-240 (1996).

Advertisement: "The first Fully Automated Digital Imaging System specifically for crystallographers—CrystalScore. Cyber Lab," ACA Newsletter 1:28 (Spring, 2000).

Baird, J.K., "Theory of protein crystal nucleation and growth controlled by solvent evaporation," J. Cryst. Growth 204:553-562 (1999).

Baldock, P., et al., "A comparison of microbatch and vapour diffusion for initial screening of crystallization conditions," J. Cryst. Growth 168:170-174 (1996).

Beckmann, W., et al., "The Effect of Additives on Nucleation: A Low Cost Automated Apparatus," J. Crystal Growth 99:1061-1064 (1990).

Berry, M.B., "Protein Crystallization: Theory and Practice," excerpts from "Structure and Dynamics of E. coli Adenylate Kinase," by Michael B. Berry (Sep. 17, 1995), 12 pages, printed from http://www.bioc.nce.edu/~berry/crystallization/crystallization.

Blow, D.M., et al., "Control of nucleation of protein crystals," Protein Sci. 3:1638-1643 (1994).

Brandt, D.W., "Multiplexed nanoliter transfers for high throughput drug screening using the Biomek 2000 and the high density replicating tool," J. Biomol. Screen 2:111-116 (1997).

Brochure: Automatic Protein Crystallization System. Douglas Instruments Limited. (1990)(4 pages).

Brodersen, D.E., et al., "Computer Programs—XAcr: a program for construction, automated setup and bookkeeping of crystallization experiments," J. Appl. Cryst. 32:1012-1016 (1999).

Bullock, E., et al., "Apparatus for the growth of crystals from small volumes of solution," J. Physics E: Sci. Instrum. 5:412-413 (1972).

Burley, S. K., "Structural genomics: beyond the Human Genome Project," Nat. Genet. 23:151-157 (1999).

Carter, C.W., "Efficient Factorial Designs and the Analysis of Macromolecular Crystal Growth Conditions," *Methods: A Companion to Meth. Enzymol.* 1(1):12-24 (1990).

Casay, G.A., et al., "Laser scattering in a hanging drop vapor diffusion apparatus for protein crystal growth in a microgravity environment," *J. Crystal Growth* 122:95-101 (1992).

Catalog, 63 pp., Hampton Research Corporation (copyright 1999).

Chayen, N.E., et al., "An Automated System for Micro-Batch Protein Crystallization and Screening," *J. Appl. Cryst.* 23:.297-302 (1990).

Chayen, N.E., "Apocrustacyanin A1 from the lobster cartenoprotein a-crystacyanin: crystallization and initial X-ray analysis involving softer X-rays," *Acta Cryst.* D56:1064-1066 (Aug. 2000).

Chayen, N.E., et al., "Conrol of nucleation in the crystallization of lysozyme," *Protein Sci.* 2:113-118 (1993).

Chayen, N.E., et al., "Fish muscle structure: fibre types in flatfish and mullet in muscles using histochemistry and antimyosin antibody labeling," J. Muscle Res. Cell Motility 14:53-542 (Oct. 1993).

Chayen, N.E., et al., "Microbatch crystallization under oil—a new technique, allowing many small-volume crystallization trials," *J. Crystal Growth* 122:176-180 (1992).

Chayen, N.E., et al., "Porous Silicon: an Effective Nucleation-inducing Material for Protein Crystallization," *J. Mol. Biol.* 312:591-595 (2001).

Chayen, N.E., et al., "Protein crystallization for genomics: towards high-throughput optimization techniques," *Acta Cryst.* D58:921-927 (2002).

Chayen, N.E., et al., "Purification, crystallization and initial X-ray analysis of the $C_1$ subunit of the astaxanthin protein, $V_{600}$, of the chondrophore *Velella velella*," *Acta Cryst.* D55:266-268 (1999).

Chayen, N.E., et al., "Space-grown crystals may prove their worth," *Nature* 398(6722):20 (1999).

Chayen, N.E., et al., "Trends and Challenges in Experimental Macromolecular Crystallography," *Quart. Rev. Biophysics* 29(3):227-278 (Aug. 1996).

Chayen, N.E., "A novel technique to control the rate of vapour diffusion, giving larger protein crystals," *J. Appl. Cryst.* 30:198-202 (1997).

Chayen, N.E., "Comparative studies of Protein Crystallization by Vapour-Diffusion and Microbatch Techniques," *Acta Cryst.* D54:8-15 (1998).

Chayen, N.E., "Protocol: A novel technique for containerless protein crystallization," *Protein Engineering* 9(10):927-929 (1990).

Chayen, N.E., "Tackling the bottleneck of protein crystallization in the post-genomic era," *Trends Biotech.* 20(3):98 (2002).

Chayen, N.E., "The role of oil in macromolecular crystallization," *Structure* 5(10):1269-1274 (1997).

Chayen, N.E., et al., "New developments of the IMPAX small-volume automated crystallization system," Acta Cryst. D50:456-458 (1994).

Cianci, M., et al., "Structure of lobster apocrustacyanin $A_1$ using softer X-rays," *Acta Cryst.* D57:1219-1229 (Apr. 2001).

Cox, M. J., et al., "An Investigation of Protein Crystallization Parameters using Successive Automated Grid Searches (SAGS)," *J. Cryst. Growth* 90(1-3):318-324 (1988).

Cox, M.J., et al., "Experiments with Automated Protein Crystallization," *J. Appl. Cryst.* 20:366-373 (1987).

Cudney, B. et al., "Screening and Optimization Strategies for Macromolecular Crystal Growth," *Acta Cryst.* D50:414-423 (1994).

D'Arcy, A., "Crystallizing Proteins—a Rational Approach?," *Acta Cryst.* D50:469-471 (1994).

DeLucas, et al., "New High-throughput Crystallization Technology," (Abstract E0014 from ACA2002 Meeting), printed from http://www.hwi.buffalo.edu/ACA on Apr. 10, 2002 (1 page).

Diller, D.J., et al., "An accurate numerical model for calculating the equilibration rate of a hanging-drop experiment," *Acta Cryst.* D55:656-663 (1999).

Dong, J., et al., "Bound-solvent structures for microgravity-, ground control-, gel- and microbatch-grown hen egg-white lysozyme crystals at 1.8 A resolution," *Acta Cryst.* D55:745-752 (Apr. 1999).

Ducruix, A., & Giege, R. (Eds.) "Crystallization of Nucliec acids and protein. 'A practical approach," (Second Eidition) Oxford: University Press (1999).

Eichoff, et al., "Development of a technology for automation and miniaturization of protein crystallization." *J. Biotech* 85(1):7-14 (2001).

Evans, P.R., et al., "Crystallographic Structure of Allosterically Inhibited Phosphofructokinase at 7A Resolution," *J. Mol. Biol.* 191:713-720 (1986).

Fiehn, H., et al., "Microsystem Technology for Pipetting Systems: Parallel Sample Treatment in the Submicroliter Range (25)," *smallTalk2000 Association for Laboratory Automation Final Conference Program*, San Diego, CA, held Jul. 8-12, 2000 (Abstract) (1 page).

Gaasterland, T., "Feasibility of Structural Genomics and Impact on Computational Biology: Post-Workshop Review," Mathematics and Computer Science Division, Argonne National Laboratory, Jan. 26, 1998 printed from http://www-fp.mcs.anl.gov/~gaasterland/sg-review. html on Apr. 12, 2002 (7 pages).

Gaasterland, T., "Structural genomics: Bioinformatics in the driver's seat," *Nat. Biotech.* 16:625-627 (Jul. 1998).

Gilliland, G. L., et al., "Screening For Crystallization Conditions and Robotics: Biological Macromolecule Crystallization Database, Version 3.0: New Features, Data and the NASA Archive for Protein Crystal Growth Data," *Acta Cryst.* D50:408-413 (1994).

Gonzalez, F., et al., "Crocodile: An Automated Apparatus for Organic Crystal Growth from Solution," *Acta Astronautica* 25(12):775-784 (1991).

Heinemann, et al., Scientific concepts: The Berlin "Protein Structure Factory initative," printed from http://www.rzpd.de/psf/s_concept2.html on Dec. 21, 2001 (16 pages).

Jancarik, J., et al., "Sparse matrix sampling: a screening method for crystallization of proteins," J. Appl. Cryst. 24:409-411 (1991).

Jing, H., et al., "New structural motifs on the chymotrypsin fold and their potential roles in complement factor B," *EMBO J.* 19(2):164-173 (2000).

Jing, H., et al., "Structural basis of profactor D activation: from a highly flexible zymogen to a novel self-inhibited serine protease, complement factor D," *Euro. Mol. Bio. Org.* 18(4):804-814 (1999).

Jing, H., et al., "Structures of Native and Complexed Complement Factor D: Implications of the Atypical His57 Conformation and Self-inhibitory Loop in the Regulation of Specific Serine Protease Activity," *J. Mol. Biol.* 282:1061-1081 (1998).

Jones, et al., "Fully Automated Preparation of Hanging Drop Protein Crystallization Plates," abstract from ACA01 meeting printed from http://www.hwi.buffalo.edu/ ACA/ACA01/abstracts/text/W0352. html on Aug. 26, 2002 (1 page).

Jones, N., et al., "Apocalypse now: update on automated protein Crystallization using the new ACA vapor diffusion plate," *Acta CrystallogrA* (1987) 43 (Supplement): C275.

Kam, et al., "On the Crystallization of Proteins," *J. Mol. Biol.* 123:539-555 (1978).

Kelders, H.A., et al., "Automated protein crystallization and a new crystal form of a subtilisin: eglin complex," *Protin Engin.* 1(4):301-303 (1987).

Koltay, P., "A Novel Fixed Volume Dispenser for the Massive Parallel Liquid Handling of Nanoliter Volumes," (Abstract for presentation scheduled for Oct. 25, 2001) printed from http://www.eurolabautomation.org on Apr. 11, 2002 (2 pages).

Korkhin, Y.M., et al., "Microseeding—Crystallization of a protein by microseeding after establishing its phase diaphragm," in Research Report 1 (Aug. 1995), printed from http://www.douglas.co.uk/rep1.html on Apr. 11, 2002 (6 pages).

Leonidas, D.D., et al., "Refined Crystal Structures of Native Human Angiogenin and Two Active Site Variants: Implications for the Unique Functional Properties of an Enzyme Involved in Neovascularization During Tumour Growth," *J. Mol. Biol.* 285:1209-1233 (1999).

Lloyd, L.F., et al., "Many Crystal Forms of Human Immunodeficiency Virus Reverse Transcriptase," *J. Mol. Biol.* 217(1):19-22 (1991).

Lowe, J., et al., "Capital Equipment MRC Laboratory of Molecular Biology Nov. 4, 2001" (4 pages).

Luft, et al., "High Throughput Protein Crystallization: Keeping up with the Genomics," (Abstract for presentation to be given at Gordon Research Conference "Diffraction Methods in Molecular Biology" on Jul. 3, 2000 at Andover, NH, USA) printed from http://www.imca.aps.anl.gov/~ahoward/luft_ab.html (1 page).
Luft, et al., "Macromolecular crystallization in a high throughput laboratory—the search phase," *J. Cryst. Growth* 232:591-595 (2001).
Luft, et al., "Microbatch macromolecular crystallization in micropipettes," *J. Cryst. Growth* 196:450-455 (1999).
Luft, et al., "Microbatch macromolecular crystallization on a thermal gradient," *J. Cryst. Growth* 196:447-449 (1999).
Luo, M., "Structural Genomics of *C. elegans*," (Abstract W0027 from ACA2002 Meeting) printed from http://www.hwl.buffalo.edu/ACA/ACA02/abstracts/text/W0027.html on Apr. 10, 2002 (1 page).
McPherson, A., "Crystallization of Macromolecules: General Principles," in *Methods in Enzymology* 114:112-120 (1985).
McPherson, A., "Crystallization of Proteins by Variation of pH or Temperature," in *Methods in Enzymology* 114:125-127 (1985).
McPherson, A., "Two approaches to the rapid screening of crystallization conditions," *J. Cryst. Growth* 122:161-167 (1992).
McPherson, A., "Use of Polyethylene Glycol in the Crystallization of Macromolecules," in *Methods in Enzymology* 114:120-125 (1985).
Meeting Summary: "NIH Protein Structure Initative Meeting: Target Selection, Feb. 1999, Washington, D.C." printed from http://www-nmr.cabm.ruters.edu/labdocuments/mtgsummaries/nih_prot_struct_init/nih on Apr. 12, 2002 (23 pages).
Meeting Summary: "NIGMS Structural Genomics Project Planning Meeting—The Protein Structure Initative, Bethedsa, MD, Nov. 24, 1998," printed from http://www-nmr.cabm.rutgers.edu/labdocuments/mtgsummaries/nigms/nigms.html on Apr. 12, 2002 (17 pages).
Montelione, G.T., et al., "Structural genomics: keystone for a Human Proteome Project," *Nat. Struct. Biol.* 6(1):11-12 (Jan. 1999).
Morris, D.W., et al., "Automation of Protein Crystallization Trials: Use of a Robot to Deliver Reagents to a Novel Multi-Chamber Vapor Diffusion Plate," *Biotechniques* 7(5):522-527 (1989).
Mueller, et al., "Development of a technology for automation and miniaturization of protein crystallization," *J. Biotech.* 85(1):7-14 (2001).
Needleman and Wunsch, "A General Method Applicable to the Search for Similarities in the Amino Acid Sequence of Two Proteins." *J Mol Biol* 48:443-453 (1970).
Newman, A.R., "Send in the Robots," *Anal. Chem.* 62(1):29-34A (1990).
News Release: "Large-scale Xn: 'The use of Microbatch for Large Scale Crystallization Projects'," Douglas Instruments, Hungerford, UK (indicated on website as news from Feb. 1999), printed from http://www.douglas.co.uk/proposal.html on Feb. 22, 2001 (5 pages).
Nyarsik, et al., "High Throughput Screening Station for Automated Protein Crystallization," (Abstract) (1 page).
Oct. 2, 2002 Press Release: "Minutes Apr. 22-23, 1999—Biological and Environmental Research Advisory Committee (BERAC)," this meeting was announced in the Federal Register for Apr. 22-23, 1999 (Public Law 92-463, 86 Stat. 770) American Geophysical Union, Washington, D.C., printed from http://www.er.doe.gov/production/ober/berac/4-99mins.html on Apr. 12, 2002 (8 pages).
Oldfield, T.J., et al., "A Flexible Approach to Automated Protein Crystallization," *J. Appl. Cryst.* 24:255-260 (1991).
Pearson and Lipman, "Improved tools for biological sequence comparison." *Proc Natl Acad Sci USA* 85:2444-2448 (Apr. 1988).
Pebay-Peyroula, E., et al., "X-ray Structure of Bacteriohodopsin at 2.5 Angstroms from Microcrystals Grown in Lipidic Cubic Phases," *Science* 277:1676-1681 (1997).
Perrakis, A., et al., "Protein microcrystals and the design of a microdiffractometer: current experience and plans at EMBL and ESRF/ID13," *Acta Cryst.* D55:1765-1770 (1999).
Presentation by Chair Graham Fleming, University of California, Berkeley: "Working Group on Biosciences," pp. 175-198, printed from http://www-als.lbl.gov/als/workshops/scidirecthtml9BioSci/Word_Work_File_L_646, index of /als/workshops/scidirecthtml/9BioSci indicates file available in multiple formats, indicates file last modified Nov. 1998.

Presentation: NASA, Marshall Space Flight Center—Lab-on-a-Chip Based Protein Crystallization, by van der Woerd, M., dated Oct. 25, 2001, printed from worldwide web in 2002 (27 pages).
Press Release: "Berkeley Lab Research Review Summer 2000—The Crystal Robot," by Preuss, P., printed from http://www.lbl.gov/ Science-Articles/Research-Review/Magazine/2000/Winter/features on Feb. 28, 2002 (3 pages).
Press Release: "Bringing the Genome to Life Report—From the Archives: Bringing the Genome to Life—Energy Related Biology in the New Genomic World. A New Research Program for the Department of Energy's Office of Biological and Environmental Research recommended by the Biological and Environmental Research Advisory Committee. (Jun. 2000)" printed from http://doegeomestolife.org/history/genome-to-life-rpt.html on Apr. 12, 2002 (23 pages).
Press Release: "Crystallomics Core @ JCSG—Crystallomics Core," printed from http:// bioinfo-core.jcsg.org/ bic/links/crystallomics.htm on Feb. 25, 2002 (2 pages with page indicating links last updated Apr. 18, 2001).
Press Release: "For Immediate Release (Sep. 25, 2000): Joint Center for Structural Genomics Funded to Advance High-Throughput Protein Structure Determination," printed from http:/www.sdsc.edu/Press/00/092600.html on Feb. 20, 2002 (3 pages).
Press Release: "Large-scale Xn—The use of Microbatch for Large-Scale Crystallization Projects," by Douglas Instruments printed from http://douglas.co.uk/products.html on Apr. 11, 2002 (5 pages).
Press Release: "Products—Products Feb. 2001," printed from http://www.douglas.co.uk/products.html on Mar. 2, 2002 (2 pages).
Press Release: "RAMC 2001—Poster Abstracts," printed from http://www.hamptonresearch.com/stuff/RAMC01/RAMC01PA.html on Apr. 10, 2002 (17 pages).
Press Release: "Research and Innovation: Genomics Institute of the Novartis Research Foundation (GNF), Novartis Institute for Genomics," (copyright, 1999) printed from http://www.pharma.novartis.com/research on Dec. 18, 2001 (2 pages).
Press Release: "Response to a Dec. 8, 2000, change from the Director of the DOE Office of Science," printed from http://www.er.doe.gov/production (19 pages).
Press Release: "System Users—IMPAX and Oryx Users Feb. 2002," printed from http://www.douglas.co.uk/users.htm on Mar. 2, 2002 (3 pages).
Press Release: "TECAN Compound dissolution—Automating Drug Discovery at Zeneca," (Oct. 1998) printed from http://www.tecan.com/pr/tec_pr_DDElisa.html on Apr. 15, 2002 (1 page).
Press Release: "TECAN GENESIS Workstation—Genesis Workstation," printed from http://www.tecan.com/tec_main_genesis_workstation.html on Apr. 15, 2002 (1 page).
Press Release: "The Robot—X-ray Crystallography in Leiden," printed fro http://www.chem.Leidemuniv.nl/bfsc/robot.html on Mar. 2, 2002 (2 pages).
Press Release: "The Scripps Research Institute—News and Views—Life After the Human Genome Project: TSRI Researchers Spearhead Protein Structure Initative," by Mika Ono Benedyk, printed from http://www.scripps.edu/newsandviews/e_20010226/print-jcsg.html on Feb. 28, 2002 (3 pages).
Press Release: "Winners—NASA Selects Research Proposals in Cellular and Macromolecular Biotechnology" printed from http://research.hq.nasa.gov/code_u/nra/current/NRA-00-HEDS-03/winners.html on Apr. 8, 2002 (5 pages).
Press Release: "PBD/Research/Research Areas/AUTOMATION," printed from http://www.lbl.gov/ LBL-Programs/pbd/xl_research/automation.html on Feb. 28, 2002 (4 pages).
Press Release: "RAMC 1999—Presentation Abstracts. Presentations T1-T16." printed from http://www.hamptonresearch.com/stuff/RAMCC99/RAMC99TA.html on Apr. 8, 2002 (11 pages).
Press Release: "RAMC 2001- Presentation Abstracts. Presentations T1-T15" printed from http://www.hamptonresearch.com/stuff/RAMC01/RAMC01TA.html on Apr. 8, 2002 (12 pages).
Press Release: "Structural Biology—Charge Jun. 10, 1997—Report of the Structural Biology Subcommittee of the Biological and Environmental Research Advisory Committee—In response to the charge letter of Dr. Martha Krebs, Jun. 10, 1997," printed from http://www.er.doe.gov/ production/ober/berac/final697.html on Feb. 26, 2002 (29 pages).

Press Release: East of England Innovation Relay Centre: Pharma—Technology Offers from Europe, particularly High-throughput protein crystallization screening and polymorph screening (Reference: PAN4159) on p. 15 of document printed from http://www.stjohns.co.uk/eeirc/pharma%/20/offers.htm on Apr. 11, 2002 (32 pages).

Press Release: Functional Genomics. http://www.bmb.psu.edu/simpson/16genome/Function.html (1 page).

Press Release: High-throughput protein crystallization screening and polymorph screening. http://www.steinbeiseuropa.de/db/ircnet_details.php?BEREICH=LIFE&TYP=Offer&BB (Abstract).

Press Release: Jaklevic et al., "Protein Microcrystallization and Structure Determination," printed from http://www.berkeleylab.com.

Press Release: LabAutomation 2001- Annual Conference and Exhibition—LabAutomation2002—Jan. 26-30, 2002—Palm Springs California—"Preliminary Poster Program" printed on Apr. 11, 2002 from http://labautomation.org/LA/LA02/program/action.lasso?-database=LA2002Abs&-layout Apr. 11, 2002d (166 pages).

Press Release: Letter to DOE Health and Environmental Research Advisory Committee Chairman dated Jun. 10, 1997, printed from http://www.er.doe.gov/production/ober/berac/97stbio.html on Feb. 26, 2002 (2 pages).

Press Release: Letter to DOE Health and Environmental Research Advisory Committee Chairman dated May 28, 1998, printed from http://www.er.doe.gov/production/ober/berac/stbiochg.html on Feb. 26, 2002 (2 pages).

Press Release: Minutes Nov. 5-6, 1998—Biological and Environmental Research Advisory Committee (BERAC). The meeting was announced in the Federal Register for Nov. 5-6, 1998 (Pub. L. No. 92-463, 66 Stat. 770) American Geophysical Union, Washington, D.C., printed from http://www.er.doe.gov/production/ober/berac/11-5-98mins.html on Apr. 12, 2002 (15 pages).

Press Release: Stewart, P.S., et al., "Using Microbatch for Large-Scale Crystallization Projects," Large-scale xn—visual—printed from http://www.douglas.co.uk/glasgow.htm Aug. 1, 2002 (3 pages).

Press Release: Structural Biology, Charge May 28, 1998—Report of the Structural Biology Subcommittee of the Biological and Environmental Research Advisory Committee—In response to the charge letter of Dr. Martha Krebs, May 28, 1998 Executive Summary—Improvements recommended for current beamlines http://www.er.doe.gov/production/ober/berac/final598.html (11 pages).

Press Release: Tecan Genesis NPS—Nanopipetting for plate and array-based applications: *Miniaturize your Application with GENESIS NPS* printed from. http://www.tecan.com/tec_main_nps.html on Apr. 13, 2002 (3 pages).

Press Release: Tecan Product News—Product News from 1998, printed from http://www.tecan.com/ tec_main_product_news_98.html on Apr. 13, 2002 (3 pages).

Press Release: Tecan Product News—Product News from 1999, printed from http://www.tecan.com/tec_main_product_news_99.html on Apr. 13, 2002 (3 pages).

Press Release: Tecan Product News—Product News from 2000, printed from http://www.tecan.com/ tec_main_news_00.html on Apr. 13, 2002 (2 pages).

Pusey M., "Growth Kinetics of Tetragonal Lysozyme Crystals," *J. Cryst. Growth* 76:593-599 (1986).

Pusey, M.L., et al., "Protein Crystal Growth—Growth Kinetics for Tetragonal Lysozyme Crystals," *J. Biol. Chem.* 261:6524-6529 (1985).

Rawas, A., et al., "Preliminary Crystallographic Studies on Duck Ovotransferrin," *J. Mol. Biol.* 208:213-214 (1989).

Report entitled, "Physical Biosciences Division," particularly section entitled "Protein Microcrystallization Robotic System," (pp. 14-17), printed from http://www-nsd.lbl.gov/LBL-Publications/LDRD/1998/PB/index.html#Jaklevic, on Aug. 28, 2002, page indicated as last modified on Feb. 19, 1999 (17 pages).

Rippon, G.D., et al., "Improved Microdroplet Method for Quantitative X-Ray Microanalysis of Small Fluid Samples," *Micron* 24(1):17-21 (1993).

Rost, B., "Marrying structure and genomics," *Structure* 6:259-263 (1998).

Rubin, B., et al., "Minimal intervention robotic protein crystallization," *J. Cryst. Growth.* 110:156-163 (1991).

Sali, A., "100,000 protein structures for the biologist," Avalon Meeting Review, document generated Jan. 22, 1998, printed Apr. 1, 1999 from http://guitar.rockefeller.edu./avalon/review/avalon.html (7 pages).

Sanchez, et al., "Protein structure modeling for structural genomics," *Nat. Struc. Biol.* (*Structural Genomics Supplement*) 986-990 (2000).

Santarsiero, B.D., et al., "Protein Micro-Crystallization Robotics System," W0251:Protein Micro-Crystallization Robotics System (09.07:Crystallization Techniques-Lectures-Room 106- Thursday, May 27 (Abstract for ACA99 meeting) printed from http://www.hwi.buffalo.edu/ACA/ACA99/abstracts/text/W0251.html on Feb. 28, 2002 (2 pages) (webpage indicates last updated on May 18, 1999).

Saridakis, E., et al., "Improving protein crystal quality by decoupling nucleation and growth in vapor diffusion," *Protein Sci.* 9:755-757 (2000).

Schuetz, et al., "A novel nano-pipetting system for the development of high quality BioChip arrays," printed from www.tecan.com/la2000_nanopip.pdf (1 page).

Section of Report entitled, "Protein Microcrystallization and Structure Determination," printed from http://www-nsd.lbl.gov/LBL-Publications/LDRD/1999/PBD.html#Stevens on Aug. 28, 2002, page indicated as last modified on Apr. 4, 2000 (3 pages).

Shapiro, L., et al., "The Argonne Structural Genomics Workshop: Lamaze class for the birth of a new science," *Structure* 6(3):265-267 (1998).

Shumate, "Low-volume (nanoliter) automated pipetting," *Am. Biotechnol. Lab.* 11(6):14 (1993).

Sibille, L., et al., "Solvent evaporation rates in the closed capillary vapor diffusion method of protein crystal growth," *J. Cryst. Growth* 110:80-88 (1991).

Smith and Waterman, "Comparison of Biosequences," *Adv Appl Math* 2:482-489 (1981).

Snell, E.H., et al., "Partial Improvement of Crystal Quality for Microgravity-Grown Apocrustacyanin $C_1$," *Acta Cryst.* D53:231-239 (1997).

Soriano, Thierry M.B., et al., "ASTEC: an Automated System for Sitting-Drop Protein Crystallization," *J. Appl. Cryst.* 26:558-562 (1993).

Stevens, et al., "Global Efforts in Structural Genomics," *Science* 294:89-92 (2001).

Stevens, "High-throughput protein crystallization." [review], *Curr. Opin. Struct. Biol.* 10(5):558-563 (2000).

Stevens, R.C., et al., Research Proposal for development and testing of a system of robotics workstations dedicated to protein crystallization., E.O. Lawrence Berkeley National Laboratory and The Scripps Research Institute, pp. 2, 29-31, 33-52 (unknown date).

Stevens, Raymond C., "Design of high-throughput methods of protein production for structural biology," Structure (with Folding & Design) 8(9):R177-R185 (Sep. 15, 2000) (Available online Sep. 8, 2000).

Stevenson, "The world of Separation Science- Lab Automation '01: A Market Preparing for transition?," pp. 4-5 (2001).

Stewart, et al., "Practical experimental design techniques for automatic and manual protein crystallization," *J. Cryst. growth* 196:665-673 (1999), printed from http://www.douglas.co.uk/rat_des.html on Mar. 2, 2002 (12 pages).

Stura, E.A., et al., "Reverse Screening," *Acta Cryst.* D50:448-455 (1994).

Swartzendruber, J.K., et al., "Apocalypse: an automated protein crystallization system. III. In the beginning: The genesis of software," (1988) p. 81, Abstract PF5, Annual Meeting of the American Crystallographic Association, Philadelphia, PA.

Tebbutt, J.S., et al., "Monitoring of crystallisation phenomena by ultrasound," *Electron. Lett.* 35(1):90-92 (1999).

Tisone, T.C., et al., "The Role of Non Contact Microfluidics in High Throughput Protein Crystallization," (Abstract W0282 from ACA2002 Meeting) printed from http://www.hwi.buffalo.edu/ACA/ACA02/abstracts/text/W0282.html on Apr. 10, 2002(1 page).

Tisone, T.C., "Dispensing systems for miniaturized diagnostics," *IVD Technology Magazine*, printed from http://devicelink.com/ivdt/archive/98 (IVDI archive, May 98).

Tutorial On: the Role of Computation Biology In High-Throughput Structure Determination: Computation Before, During, and After Structural Genomics, document dated Feb. 17, 1998, printed Apr. 1, 1999 from http://www.fp.mcs.anl.gov/gaasterland/sq-review-slides.htm; (14 pages).

van der Woerd, M., et al., "About Small Streams and Shiny Rocks: Macromolecular Crystal Growth in Microfluidics," (Abstract W0210 from ACA2002 Meeting) printed from http://www.hwi.buffalo.edu/ACA/ACA02/abstracts/text/W0210.html.

van der Woerd, "Lab-on-a-chip Based Protein Crystallization [P-66]," *smallTalk 2001 Association for Laboratory Automation Final Conference Program*, San Diego, CA, held Aug. 27-31, 2001 (Abstract) (2 pages).

Varadarajan, R., et al., "Crystallographic Structures of Ribonuclease S Variants with Nonpolar Substitution at Position 13: Packing and Cavities," *Biochem.* 31(49):12315-12326 (1992).

Villasenor, et al., "Fast Drops: A Speedy Approach to Setting Up Protein Crystallization Trials," (Abstract W0309) from ACA01 meeting printed from http://www.hwi.buffalo.edu/ ACA/ACA01/abstracts/text/W0309.html on Dec. 21, 2001 (1 page).

Ward, K.B., et al., "Automatic Preparation of Protein Crystals Using Laboratory Robotics and Automated Visual Inspection," *J. Cryst. Growth* 90:325-339 (1988).

Ward, K.B., et al., "Automating crystallization experiments," in Crystallization of Nucleic Acids and Proteins: A Practical Approach eds. A. Ducruiz & R. Giege, Oxford Univ. Press, New York, pp. 291-310.

Weber, P.C., "Overview of Protein Crystallization Methods," *Methods in Enzymology* 276:13-22 (1997).

Weber, P.C., et al., "Experiments with automated protein crystal growth," (1987) p. 28, Abstract H5, Annual Meeting of the American Crystallographic Association, Philadelphia, PA.

Webpage: "Harvesting, Harvesting Crystals from Microbatch for Cryocrystallography," Douglas Instruments—Research Report 3, Oct. 1995, printed from http://www.douglas.co.uk/rep3.htm on Apr. 11, 2002 (4 pages).

Webpage: "Poster Session 7—Genomics, Proteomics and New Target Discovery," The Society for Biomolecular Screening ~7th Annual Conference and Exhibition (2001), see #7014-7015, printed from http://www.hwi.buffalo.edu/ (5 pages).

Webpage Eickhoff, et al., "An Automated Platform for Miniaturized protein crystallization," Greiner Bio-One (Abstract), date of last modification on web indicated as Mar. 30, 2001, printed May 2002 (1 page).

Website listing Abstracts for Oral Presentations: S7—Instrumentation—Instrumentation and Techniques for crystallization. pp. 1-3 (Nancy 2000 XIX European Crystallographic Meeting (held Aug. 25-31).

Website listing products available from Gilson, presented from http://www.gilson.com/cyberprd.htm on Feb. 22, 2001 (1 page).

Website: "A day on High-Throughput Techniques in Structural Biology," printed from http://www.embl-heidleberg.de./courses/StructureSolution02/satellite.html (5 pages) text dated Aug. 1998 and Feb. 1999.

Website: "A Recipe to grow crystals of lysozyme by the gel acupuncture technique: Granada Crystallization Box," printed from http://lec.ugr.es/GranadaCrsytBox/GCB on Apr. 11, 2002 (7 pages).

Website: "Differences—The Major Differences between Oryx 6 and IMPAX 1-5," Douglas Instruments, dated Mar. 2001, printed from http://www.douglas.co.uk/differen1.htm on Apr. 11, 2002 (1 page).

Website: "General Interest II—Invited Abstracts," (Jul. 26, 2001) printed from http://www.hwi.buffalo.edu/ACA/CA01/abstracts on Apr. 13, 2002 (2 pages).

Website: "Harima Workshop on Implementation for High-throughput Structure Determination by Protein Crystallography—Present Status and Future Goal- A Satellite of International Conference on Structural Genomics 2000 at Spring-8." printed from http://www.spring8.or.jp/english/conference on Dec 19, 2001 (4 pages).

Website: "News" printed from http://www.douglas.co.uk/news.htm on Apr. 15, 2002 (2 pages).

Website: "Nobel Prize—User Prize" printed from http://www.douglas.co.uk/walker.htm on Mar. 2, 2002 (1 Page).

Website: "Oryx 6—Using Oryx 6 for Crystallization with Microbatch: Microbatch operation in identical to IMPAX 1-5" printed from http://www.douglas.co.uk/oryx.htm.

Website: "PhysicsWeb—Protein cystallography: the human genome in 3-D," http://physicsweb.org/article/world/11/5/8 (May 1998), printed from website Apr. 11, 2002 (9 pages).

Website: "Publication—Journals—Trade Journals: Events Index-Abstracts and Proceedings—Achema 2000," printed from http://www.combichem.net/files/abstract1.htm on Aug. 1, 2002 (18 pages).

Website: "Impax: IMPAX 1-5 for Crystallization with Microbatch" printed from http://www.douglas.co.uk/impax.htm on Mar. 2, 2002.

Website: *Bio*Robotics http://www.biorobotics.com (Pamphlet), printed on Oct. 7, 1999 (12 pages).

Website: Micro-Arraying with the *Micro* Grid http://www.biorobotics.com/MicroArray.html, printed Oct. 20, 1999 6 pages).

Wilson, S.A., et al., "Crystallization of and Preliminary X-ray Data for the Negative Regulator (AmiC) of the Amidase Operion of *Pseudomonas aeruginosa,*" *J. Mol. Biol.* 222(4):869-871 (1991).

Yakovlev, Y.O., et al., "A Laboratory Apparatus for Crystal Growth from Solution," *Instruments and Exp. Tech.* 41(2):292-296 (1998).

Yegian, D., "Task-specific robotics for sample loading, centering and retrieval," printed from http://smb.slac.stanford.edu/jcsg/robotics/abstracts/dy_abs.html on Apr. 12, 2002 (1 page) (site last modified Oct. 16, 2000).

Zeelen, J. Ph., et al., "Crystallization Experiments with 2-Enoyl-CoA Hydratase, Using an Automated 'Fast-Screening' Crystallization Protocol," *Acta Cryst.* D50:443-447 (1994).

Zeppezauer, M., "Microdiffusion cells for the growth of single protein crystals by means of equilibrium dialysis," *Arch. Biochem. Biophys.* (1968) 564-573.

METHOD FOR PREPARATION OF MICROARRAYS FOR SCREENING OF CRYSTAL GROWTH CONDITIONS

CROSS REFERENCE TO RELATED APPLICATIONS

This application claims the benefit of priority of (1) U.S. Provisional Application No. 60/344,581, filed Oct. 23, 2001; and (2) is a continuation-in-part of U.S. application Ser. No. 10/208,576, filed Jul. 30, 2002, which claims priority to U.S. Provisional Application No. 60/308,698, filed Jul. 30, 2001, and U.S. Provisional Application Ser. No. 60/328,958, filed Oct. 12, 2001, and which is a continuation-in-part of U.S. application Ser. Nos. 10/160,572, 10/160,906, 10/161,141, each of which were filed on May 30, 2002, each of which were continuing applications of U.S. application Ser. No. 09/543,326, filed Apr. 5, 2000, hereby incorporated in its entirety by reference, which claims benefit of U.S. Provisional Application No. 60/128,018, filed Apr. 6, 1999; and (3) is a continuation-in-part of U.S. application Ser. No. 09/947,655, filed Sep. 6, 2001, which is a continuation-in-part of U.S. application Ser. No. 09/543,326, filed Apr. 5, 2000 (now abandoned), which claims priority to U.S. Provisional Application No. 60/128,018, filed Apr. 6, 1999, all of which are hereby incorporated in their entirety herein by reference.

BACKGROUND

1. Field of the Invention

The present invention generally relates to the crystallization of macromolecules such as proteins from solutions. The present invention is particularly related to the preparation of arrays of solutions useful for screening crystallization conditions to determine which conditions are optimal for the crystallization of macromolecules. Even more particularly, the present invention is related to preferred techniques of preparing solutions suitable for screening, and for the screening conditions themselves, where the total macromolecule solution volume is very small, typically in nanoliter quantities or below.

2. Background of the Invention

The crystallization of macromolecules, especially of biological macromolecules, is an important activity in many fields. Obtaining high quality crystals of any given macromolecule typically enables subsequent solution of the macromolecule's three dimensional structure (atomic configuration) using diffraction techniques. Of particular interest, the three dimensional structures so obtained can be of paramount importance in the rational design of drugs or other therapeutics. Additionally, it is commonly accepted that one of the primary benefits that will flow from elucidation of the genome will be an improved understanding gained of the proteome, the entire set of expressed proteins in a particular biological organism. However, the full advantage that can be gained from that improved understanding of the proteome can only be realized with the knowledge of the three dimensional atomic configuration of each substituent protein. For example, a knowledge of the three dimensional atomic configuration of a given protein, referred to herein as its active conformation, will provide opportunities to use computerized methods and techniques, among others, to design drug molecules that will effectively and/or efficiently interact with the target protein.

The orderly crystallization of macromolecules from a solution containing the macromolecules results from complex interplay between many variables, including process kinetics (the rate at which the solution approaches supersaturation conditions), pH, ionic composition of buffer components in the solution, the type and concentration of crystallization agents, temperature, etc. As a result, the process of determining what conditions are suitable for crystallizing a given macromolecule is formidable. Typically, hundreds or thousands of experiments are conducted in which one or more of these variables is different from those of one or more of the others. This process, often referred to as screening, is useful to identify the best conditions to use in order to obtain high quality crystals. Usually, once screening has identified suitable conditions, further experiments are performed with those conditions so identified to obtain large crystals for subsequent diffraction studies.

The advent of the genomics and proteomics age has resulted in an unprecedented increase in the number of biological macromolecules available for crystallization. However, due to technical difficulties in expressing and purifying many proteins, the amount of protein available for screening crystallization conditions is often not adequate to provide for screening a suitable number of crystallization conditions if conventional methods of screening are used. This can be illustrated by typical circumstances encountered where only sub-milligram amounts of proteins are available, but it is desirable to screen hundreds or thousands of different conditions. For screening such a large number of conditions with such a small amount of a protein, each screening experiment must use no more than a nanogram of protein. Ideally, each screening experiment would use even less protein. As typical supersaturation levels of proteins in solution are much higher than those corresponding to small molecular weight compounds, the volume of the solution in which the experiment must be carried out, in order to achieve supersaturating concentrations, must be very small. Examples of the small volumes required are typically less than or equal to a few hundred, a hundred, fifty, twenty-five, ten, five or one nanoliter(s).

Conducting screening experiments of macromolecules, in particular of those biological macromolecues, are further constrained by factors in addition to the quantity of protein required. These further constraints include those related to the types of solutions used, the accuracy requirements, the means necessary to dispense small volumes of various components, and limitations on the techniques that can be used for practical manipulation of small volumes. Each of these additional constraints must be overcome in order to allow the screening in low volumes to lessen the quantity of protein required. It would be further desirable to provide such methods that address each of these particular constraints in a manner that allows high levels of flexibility, accuracy, precision and reproducibility. Furthermore, it would be an advantage if the methods so provided were simple to use.

SUMMARY OF THE INVENTION

In accordance with the purpose(s) of this invention, as embodied and broadly described herein, this invention, in one aspect, relates to methods for the screening of crystallization conditions in small solution volumes. In particular, the method provides improvements that resolve certain technical aspects that impede the use of arrays of experimental conditions.

In one aspect of the present invention, solutions used in the crystallization screens, such as protein, buffer or precipitant solutions, can be prepared in larger volumes than are used in each individual crystallization screening reaction. The preparation and mixing of the solutions using water, buffers, and various crystallization agents can be performed using automated robotic dispensing systems. The volume of the solutions prepared can be greater than 10, 50, 100, 200, 300, 500, 750 or 1000 microliters. The volume of the solutions prepared can also be less than 50, 100, 200, 300, 500, 750, 1000 or 2000 microliters. The solutions, once prepared, can be stored for a period of time prior to their use in the crystallization condition screening experiments. Alternatively, the solutions can be prepared as needed prior to their use in the crystallization screening experiments.

The solutions can be prepared, and/or stored in multi-well plates as are known to those of skill in the art. Examples of these multi-well plates include, but are not limited to, 96 well plates and 384 well plates. The sets of solutions prepared are referred to herein as recipe libraries.

The individual solutions themselves, also referred to herein as recipes or recipe solutions, can be more dilute than is typical in crystallization conditions used in normal, larger volume formats. For example, it is typical in the art to provide solutions that contain a greater percentage of volatile solvent than is required and/or which allows precipitation and/or crystallization. As is understood by those of skill in the art, for precipitation and/or crystallization to occur, evaporation of some volume of the solvent is required. Alternatively, the removal of solvent by some other method (e.g., absorption, dialysis, or other methods as are known to those of skill in the art) with the consequent concentration of protein and or precipitant agent can substitute for loss of solvent by evaporation.

The present invention includes the use of protein solutions, precipitant solutions, and recipe solutions containing greater percentages of volatile solvent and/or lower concentrations of constituents required for precipitation and/or crystallization than is used by those processes that have been used. If the volume of solvent at the point at which crystallization occurs is 100%, the volume of solvent present in the recipes is greater than 110, 120, 130, 140, 150, 160, 170, 180, 190, 200, 220, 250, 300, 350, 400, 450 or 500%. The volatile solvent can be water or other solvents as are known to those of skill in the art. Other solvents can be mixtures of more than one solvent, composition or compound.

In another aspect, the system provided by the present invention includes the use of an automated fluid manipulation system. The automated fluid manipulation system can take recipe solutions from a recipe library and transfer these to other formats. This reformatting can be done to create different recipe libraries or can be used to replicate large numbers of low-volume libraries in multiwell plates. It is contemplated that these multiwell plates can be adapted for use by automated and/or high-throughput machinery other than that machinery described herein. The automated fluid manipulation system of the present invention can include multiple dispensing tips arranged on a single dispense head or can include single or multiple dispensing tips arranged on more than one dispense head. For example, the system can include 2, 3, 4, 6, 8, 10, 12, 16, 20, 24, 32, 40, 48, 56, 64, 72, 80, 88 or 96 dispensing tips. The tips can be arranged on one, two, three, four, five, six or eight dispensing heads.

In yet another aspect, the invention provides an automated crystallization system. The provided system can take up a fluid component from a selected volume, and can also dispense a fluid component to a selected volume. In particular aspects, the machinery of the invention can aspirate and dispense protein solution droplets and/or recipe solution droplets into at least 10, 20, 50, 100, 200, 400, 600 or 1000 wells in a multi-well plate. The volume of the protein and/or recipe solutions that can be dispensed can be less than 1, 2, 5, 10, 20, 30, 50, 75, 100, 150, 300, 500 or 1000 nanoliters. The volume of the protein and/or recipe solutions that can be dispensed can be greater than 10, 20, 30, 50, 75, 100, 200, 300, 400, 500, 600, 700, 800, 900 or 1000 picoliters, and greater than 2, 3, 5, 10, 20, 30, 50, 75, 100, 150, 300, 500, 700 or 900 nanoliters. Once volumes of proteins and/or recipe solutions are dispensed into a plurality of wells in a multi-well plate, the respective solutions in the wells can be quickly covered with an oil mixture. Optionally, the entire well plate, or portions of the well plate can be covered with a covering. Examples of a covering include, but are not limited to, those made from plastic compositions such as tape. If tape is used, the tape can be a polymer such as, but not limited to, Teflon. Optionally, the plate can be cooled below room temperature to minimize or control evaporation. Optionally, the relative humidity of the environment within which the plate is contained can be raised to minimize or control evaporation.

In a particular embodiment of the invention, the crystallization system includes a first recipe solution preparation and storage sub-system used to prepare a plurality of recipe solutions for storage until the recipe solutions are required for use within the crystallization system, and a second aspiration and dispensing sub-system used to aspirate and dispense a plurality of protein solutions and of the recipe solutions, respectively, into a plurality of wells.

In another embodiment, a crystallization experiment preparation system can include: a dispense head provided with plurality of fluid dispenser tips; a video camera and a long range microscope each carried on said dispense head; a stage constructed and arranged to move the dispense head, the video camera, and the long range microscope together in the X, the Y, and the Z directions, respectively; a deck area positioned with respect to the stage, said deck area having at least one fixture for receiving at least one recipe plate, at least one protein plate, at least one crystallization plate, a quality control area, and a wash system, respectively, thereon.

In another embodiment, a crystallization experiment preparation system can include: a dispense head provided with plurality of fluid dispenser tips; a video camera and a long range microscope each carried on said dispense head; a deck area positioned with respect to the dispense head, said deck area having at least one fixture for receiving at least one recipe plate, at least one protein plate, at least one crystallization plate, a quality control area, and a wash system, respectively, thereon, wherein the dispense head, the video camera, and the long range microscope are held together in a stationary position with respect to a deck area; and wherein the deck area is constructed and arranged to be moved with respect to the dispense head, the video camera, and the long range microscope by a stage movable in the X, the Y, and the Z, directions, respectively.

In another embodiment, a crystallization experiment preparation system can include: a dispense head provided with plurality of fluid dispenser tips; a video camera and a long range microscope each carried on said dispense head; a first stage on which the dispense head is positioned, said first stage being constructed and arranged to move the dispense head in the Z direction; a deck area positioned with respect to the dispense head, said deck area having at least one fixture for receiving at least one recipe plate, at least one protein plate, at least one crystallization plate, a quality control area, and a wash system, respectively, thereon; and a second stage adapted to carry said deck area in the X and the Y directions, respectively.

The protein and/or recipe solutions provided can be used for screening crystallization conditions using a number of different methods of crystallizing proteins from solutions. These methods include, but are not limited to, batch crystallization wherein the protein and precipitant-containing recipe solutions are mixed together, and those methods wherein the protein solution and precipitant-containing solution, recipe solutions, are kept physically separate but in fluid communication with one another. Methods wherein the fluid communication is liquid-liquid, liquid-vapor or vapor-vapor are therefore contemplated.

In a particular embodiment, the method for screening protein crystal growth conditions can include: providing a microarray with a plurality of wells in the microarray; dispensing a volume of protein solution containing a protein into at least one of the wells; dispensing a recipe solution into at least one of the wells, wherein the recipe solution was prepared from bulk ingredients prior to being dispensed into the wells and was stored in a plurality of containers or in a second multiwell plate; subjecting the protein solution, or a combination solution formed by the combination of the protein solution with the recipe solution, to environmental conditions effective to form protein crystals; and observing the growth of protein crystals or precipitation of protein.

In another particular embodiment, the method for screening protein crystal growth conditions can include: providing an array of at least two wells; dispensing a volume of protein solution containing a protein into at least one of the wells; dispensing a recipe solution into at least one of the wells, wherein the recipe solution was prepared from bulk ingredients prior to being dispensed into the wells and was stored in at least one of a plurality of containers or in a second multiwell plate; subjecting the protein solution, or a combination solution formed by the combination of the protein solution with the recipe solution, to environmental conditions effective to form protein crystals; and observing the growth of protein crystals or precipitation of protein.

In one preferred method, referred to as the modified vapor diffusion process, the protein solution is placed in a second well near a first well. The first well is filled with a recipe solution and the second well is filled with a mixture of the protein solution and a smaller amount of the recipe solution than is present in the first well. A mixture of oils can be used to cover the first and/or second wells. The plate in which the first and second wells, respectively, or any number of first and second well pairs, are formed can be sealed with a clear cover or tape. Each well pair can be interconnected with a channel providing for vapor contact between each pair of first and second wells.

In another preferred method, an under-oil process, solutions in wells are overlayed with an oil, mixture of oils, or composition containing oil. Solutions so overlayed, or wells containing such solutions, or plates containing wells can be further sealed with a cover. The cover used can be a clear cover. The cover used can be tape.

In another aspect, the invention provides for the proper sequence with which the recipe and protein solutions are dispensed. In a preferred method, the protein solution is dispensed prior to, simultaneously with, or after the recipe solution is dispensed. If the dispensing of the protein and recipe solutions is not substantially simultaneous, i.e., separated by less than 1, 2, 3 or 5 minutes, the dispensing can be separated by greater than 1, 2, 3, 5, 10, 15, 20, 30, 60, 90, 240, 360, 480, 720, or 1200 minutes, or may be separated by less than 2400, 1200, 720, 480, 360, 240, 90, 60, 30, 20, 15, 10, 5, 3 or 2 minutes.

In still another aspect, the invention provides a method by which accurate dispensing and formulation of solutions is achieved. In a specific embodiment, accurate dispensing of volumes is achieved by use of larger dispensed volumes.

In another aspect, the invention provides a method used to control the initial rapid evaporation rate from the droplets.

In another aspect, the invention provides for the slow evaporation rate that is required for the orderly growth of crystals.

One particularly important aspect of the present invention is the use of dilute solutions which require significant loss of solvent prior to crystallization occurring.

Additional advantages of the invention will be set forth in part in the description which follows or may be learned by practice of the invention. The advantages of the invention will be realized and attained by means of the elements and combinations particularly pointed out in the appended claims. It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate (one) several embodiment(s) of the invention and together with the description, serve to explain the principles of the invention.

DETAILED DESCRIPTION

Figure 1:
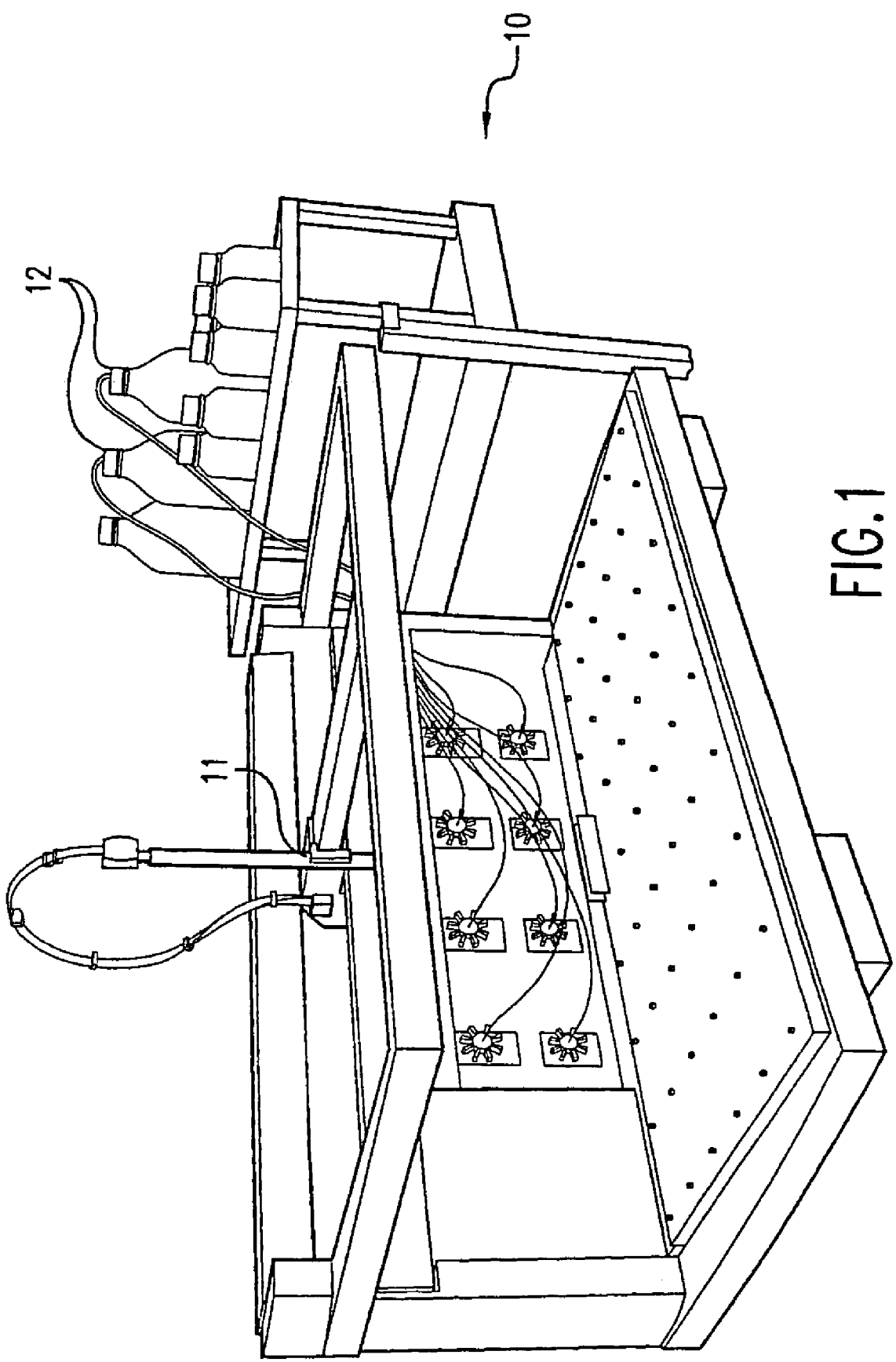
FIG. 1 is a depiction of the recipe solutions preparation system, the RecipeMaker device. The RecipeMaker in this figure is comprised of a robotic liquid handler with 8 probes, 8 computer-controlled syringes, and 8 computer-controlled distribution valves. Computer control of the devices is achieved by use of computer with custom control software directing the actions to be taken by the devices of the invention.

The present invention may be understood more readily by reference to the following detailed description of preferred embodiments of the invention and the Examples included therein, and to the Figures and their previous and following description.

Before the present compounds, compositions, articles, devices, and/or methods are disclosed and described, it is to be understood that this invention is not limited to specific methods, specific solutions, or to particular devices, as such may, of course, vary. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Thus, for example, reference to "a precipitant" includes mixtures of a precipitant, reference to "a solution" includes combination of and/or mixtures of two or more such solutions, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

One method provided by the present invention is an improvement over previous methods for screening of plurality of solution conditions in low volumes to determine those conditions that lead to crystallization of macromolecules, and in particular, of biological macromolecules. Preferably, the quantity of the biological macromolecule that is used for each experiment is in the microgram, nanogram, or picogram range, and the preferred volume of the solution is in the picoliter or nanoliter range. It will be appreciated by those skilled in the art that the particular volumes and amounts of protein or solution ingredients employed will vary without limitation according to the protein, its concentration, and the desired experimental protocol. As used herein, the term "macromolecule" is meant to include all naturally occurring and synthetic peptides, polypeptides, proteins, protein complexes, and polymers.

Crystallization of macromolecules from solutions occurs when the concentration of the macromolecule exceeds the maximum concentration allowable in solution that is dictated by the thermodynamics of the macromolecule solution. While phase transitions from a solution to a solid state always occur with increasing concentration, orderly growth of the solid in a highly order crystalline form does not. Crystal growth of macromolecules is a special form of phase transition that is very difficult to achieve in practice. Consequently, those of skill in the art seeking to promote crystal growth generally conduct multiple experiments with a plurality of solution conditions that include variations in the type, strength, and quantity of buffers, the pH, temperature, and the type and quantity of different additives collectively referred to as crystallization agents. The concentrations of these components are often quite low, sometimes less than one percent of the total volume of the solution. For example, surfactants typically used for crystallization of membrane-bound proteins are generally present at very low concentrations. In addition, the concentrations of these components are often quite critical in the success or failure of crystal growth. Normally, when crystallization screening is conducted according to general practices, screening condition trials are prepared by dispensing the various ingredients directly from their bulk solutions forming droplets which are typically of several microliters in volume.

However, when the volume of each trial condition tested is too low, the precision and accuracy required of the dispensing devices used to deliver volumes of each component is greater than that available with current technology. This is particularly true when experiments are conducted in nanoliter range, or lower, volumes and for those experiments wherein solution components are required in low concentrations. For example, trials containing one percent surfactant in a fifty nanoliter droplet require the accurate and repeatable delivery of one half of a nanoliter of 100% surfactant. While certain modern dispensing technologies, in particular those employing piezo driven capillaries, are capable of delivering such volumes accurately and with adequate precision, the wide variation in viscosity and surface tension of solution ingredients results in significant difficulties in realizing the theoretically available precision needed for high throughput low volume experiments.

However, as described herein, the present invention obviates many of the difficulties arising from the differences in surface tension viscosity and the like. Specifically, the present method, by combining larger volumes of components to form the recipe solutions, allows accurate dispensing and formulation of solutions which can then be dispensed in smaller volumes to form the crystallization reactions. Because the differences in the properties of the different recipe solutions are of a significantly lower magnitude than the differences in the properties of the component solutions normally dispensed to form crystallization reactions, realizing an appropriately high level of accuracy and precision is attainable by formulating solutions using the presently disclosed method.

In one aspect of the present invention, the preparation of the plurality of protein and/or recipe solutions that are subsequently used in crystallization condition screening experiments is separate from the step of actually preparing the crystallization condition trials. A large number of individual solutions representing a plurality of ingredients can be prepared by an automated dispensing system. The dispensing system may comprise a commercially available computerized robotic dispenser in which one or more dispensing probes are connected to reservoirs containing the bulk ingredient solutions. Depending on the number of the bulk solutions required, and the number of available dispensing probes, it is possible that there may be more bulk solutions required than there are dispensing probes. When this is the case, computerized distribution valves can be used to switch among the ingredients, thereby allowing for the dispensing of a greater number of different bulk solutions than the number of dispensing probes.

Computer programs or other electronic media can be used to direct the action of the automated dispensing system used to prepare the protein and recipe solutions. The computer programs and/or electronic media can include data indicating which bulk ingredients are required in each solution, and can command the dispensing system to dispense specified volumes from each tip/valve combination such that the total volume of all ingredients in the each well is the same or as otherwise desired. Using this method, in which the total protein/recipe solution volume is preferably in the milliliter range, provides for less stringent operational requirements from the dispenser to achieve the correct proportions of ingredients in the solution. A plurality of the solutions can be prepared in standard multi-well plates, sealed, and shelved until equilibration occurs (typically a day or less). If quicker equilibration of the solutions is desired, the sealed plates, also referred to as bulk recipe libraries, can be mixed using mechanical means known to those skilled in the art including, but not limited to, vortexing and shaking.

Because the automated dispensing system of the present invention that is used to prepare the protein and recipe solutions does so in larger, i.e., preferably greater than nanoliter or more preferably greater than microliter volumes, many dispensing technologies can be used effectively with the required level of accuracy and precision. The dispensing technologies, well known to those of skill in the art, include, but are not limited to, positive displacement pumps, aerosol systems, devices using ink-jet technologies, and piezo-electrically actuated dispensing devices. The manufacture and use of such devices are well within the skill and knowledge of those of ordinary skill in the art.

Once prepared by use of the devices and methods of the present invention, the bulk recipe libraries can be further manipulated. Using the same robotic dispenser used to generate the bulk recipe libraries, or a second dispenser if so desired, the bulk recipe libraries can be reformatted into smaller volume multi-well plates. It is preferred that this reformatting be carried-out only after equilibration or mixing of the larger bulk recipe libraries. The smaller volume multi-well plates can be sealed following reformatting. For example, a bulk recipe library, prepared in 2 milliliter 96 deep well plates, can be re-formatted into 80 microliter 384 well plates. One advantage to this procedure is that it allows crystallization experiments to be conducted in volumes significantly smaller than can be prepared, and/or that the dispensing requirements are not as stringent as they would be otherwise. Further, because the bulk recipe library is first re-formatted into a plurality of low volume plates, the exposure of solvents containing volatile ingredients does not inordinately affect the reproducibility between different sample volumes and/or sample plates. In practice, a bulk recipe library is first re-formatted into a plurality of low volumes plates, which are then used as needed and discarded. Devices and methods suitable for reformatting solutions will typically be those that more accurately and precisely dispense small volumes. Examples of such devices and methods, including the factors to be considered in their design and use, are well-known to those of skill in the art as is illustrated by commentary entitled, "Liquid Handling Advances Boost Lab Productivity," published in The Scientist 9[11] on May 29, 1995, which is incorporated herein by references for its teachings relating to automated fluid distribution. Other relevant publications and patents relating to aspects of the technology required for optimization of the present invention include; "Dispensing Systems for Miniaturized Diagnostics" published in IVD Technology in May, 1998; and "Nanoliter Dispensing published in Drug Discovery & Development in June, 2002; and references cited therein, each of which is incorporated herein by reference in its entirety for the purpose of describing features of the devices and methods of the present invention related to accurately and precisely dispensing a plurality of small volumes. Further, automated devices that can be used to practice the present invention or that can be adapted to practice the present invention can be obtained from many different manufacturers. Examples of devices that can be used or adapted for use include, but are not limited to, those available from Hamilton, Nanoliter, PerkinElmer Life Sciences, Robbins Scientific, Tecan, Cartesian Technologies, Innovadyne, Gilson, and Zymark.

Simultaneously with this procedure of separating the preparation of recipe solutions and the screening experiments themselves, the advantages of increased reproducibility and lowered volume requirements result in further advantages, which include the adaptability of the process to standard robotic dispensers, the minimization of recipe variation due to evaporation of volatile ingredients when re-formatting is used, and increased flexibility for high throughput operations that are inherent in the off-line preparation of recipe libraries that may be stored and used as needed. Examples of related types of devices that utilize the ability to dispense small volumes to prepare samples are known to those of skill in the art. For examples of these related types of devices, necessary parameters needed for their effective operation and teachings adequate to allow those of skill in the art to make and use the devices of the invention, portions of U.S. Pat. Nos. 6,296,811; 6,387,273; 6,423,536; and 6,296,673 and all references cited therein relevant to dispensing devices and automation of dispensing devices, is incorporated herein by reference.

In the present invention, the crystallization experiments are conducted using an automated robotic dispenser constructed means arranged to quantitatively dispense nanoliter and microliter volume aliquots. A robotic dispenser in accordance with the present invention thus comprises several distinct components. In a preferred embodiment, these components include, but are not limited to, fast solenoid dispensing systems that use a constant back pressure with an array of dispenser tips, switching valve systems to allow for the computerized syringe aspiration of the recipe and protein solutions and the dispensing of the same, an XYZ directional table providing for the exact placement of the dispenser tips, a deck area with designated locations for the protein solution source plate, the recipe library plate, and the experiment plate thereon, as well as, quality control and wash stations for the dispenser tips, machine vision systems comprising a video camera and a long range microscope lens, and computer controller units.

Dispensing technologies currently available for operations in low solution volumes have distinct limitations for applications that require dispensing arbitrary recipe solutions, each with different properties, as is required for producing solutions in extremely low volumes. Piezo devices, as used herein, are those that utilize the piezoelectric effect to dispense a fluid, namely, they are devices which include a component such that when a voltage is applied across a certain surface of a solid, the solid undergoes a mechanical distortion. For example, the piezo devices can comprise a small diameter glass capillary surrounded by piezoelectric material which, if subjected to the application or removal of a voltage, results in constriction of the capillary tube. The constriction of the capillary tube causes ejection of a droplet from the end of the capillary tube. Such piezo dispensing devices are highly accurate, but since they rely on surface wave excitation, they must be re-calibrated whenever the different fluids to be dispensed have significant differences in surface tension and/or viscosity. Pin-based dispensing technologies are less quantitative and suffer from high variability for different liquids. Fast solenoid technologies, as used herein, includes those which rely on a two step process in which, during the first step, a valve is open which allows a small amount of liquid to be pushed out of a small orifice at the end of the dispenser tip; and in the second step the valve is rapidly closed which freezes the motion of the liquid in the tube connecting the valve to the tip.

The dispensing which occurs with fast solenoid technology processes occurs when the kinetic energy of the rapidly moving liquid that is already outside the orifice exceeds the energy necessary to overcome the integrated surface energy of the liquid jet at the edge of the orifice. The use of fast solenoid technology provides significant advantages and is a preferred method of use within the current invention. It is believed that fast solenoid dispensing will provide a means for accurately dispensing a wide range of liquids of different properties, as defined by their different surface tensions and viscosity values. For many solutions which can be used in the practice of the invention, this capability can be important as many prepared recipe solutions may have high viscosity and/or surface tension values. Importantly, however, the use of the presently disclosed method of preparing recipe solutions in larger volumes and then redistributing these as needed greatly reduces the variability associated with differences in physical properties as the final recipe solutions prepared that will be redistributed in the smaller volumes, where differences in factors such as viscosity are so relevant, will be minimized. Furthermore, the small differences that do occur can be minimized or adjusted for in the present invention. Specifically, devices of the present invention can be calibrated in accordance with the knowledge and understanding of those of skill in the art of automated or mechanical dispensing of fluids.

The calibration of individual dispenser tips used to dispense fluids can be used to provide uniform dispensing from an array of such tips. If the dispenser tips are to be calibrated, a machine vision system can be used. For example, the apparatus of the invention can be used to dispense sets of droplets of presumed volumes, the actual volumes dispensed can then be measured, and a calibration curve can be constructed for each individual dispensing tip system allowing for the proper adjustment of the dispensing apparatus. As is understood by those of skill in the art, these methods can encompass reiteration for optimization of accuracy and/or precision. Employing individual dispenser tip calibration during the operation of the apparatus for the practice of the invention provides for a low coefficient of variation amongst the tips and improves the overall accuracy and/or precision. These advantages of higher precision and greater accuracy can be accomplished even when a variety and/or a multiplicity of dispenser tips are used. Methods of measuring volumes actually dispensed include visual inspection, determination of mass, and other means. For example, a solution of a light absorbing or fluorescent dye of known concentration can be dispensed, and the actual volume dispensed can then be determined by use of absorbance or fluorimetric techniques.

In another aspect, the invention provides a method of conducting crystallization experiments in a droplet containing the protein and the recipe solutions, wherein the droplet is covered by oil of various compositions. The oil, when so used, can be to control a slow transport of water from the droplet through the oil and into the surrounding environment. Slow transport provided by the coverage of the droplet by the oil allows for a slower loss of solvent and concomitantly a slower increase in the concentrations of the protein and other recipe ingredients than is possible when the droplet is not covered. This slower increase in protein and/or recipe ingredient concentration is preferable for orderly crystal growth. Pure oils or mixtures of oils such as silicone and paraffin can be used to allow for rapid to very slow water diffusion rates from the droplet. In the present invention, layering oil over low volume droplets shortly after they are dispensed arrests the rapid evaporation of water, which, if left unchecked, would result in the loss of too much moisture from the droplets in too short a time. In addition, once droplets are covered with oil, it is not necessary to cover each well with other means as rapidly as would otherwise be required. Thus oil coverage provides two distinct advantages, the first is unique to low volume dispensing (by arresting the rapid uncontrolled evaporation after dispensing), and the second is similar to previous experimental techniques in which oils are used to control the slow transport of water and the process kinetic rate. If a mixture of oils is used, the fraction of particular oils can be varied in accordance with necessary requirements to confer desired properties to the mixture of oils.

In an alternative embodiment, the use of oil to immediately cover droplets following their dispensing can be used in conjunction with crystallization trials carried-out using the vapor diffusion process. In this case, oils that are highly permeable to water, such as silicone oil, are preferred as their use arrests the rapid evaporation of the small protein and recipe droplet, while allowing for the actual process kinetics to proceed in a rate similar to standard vapor diffusion experiments. In certain embodiments, a mixture of oils can be used. For example, the oil can be a mixture of silicone and paraffin oil. The oil can be chosen or the mixture of oils can be selected so as to modulate its characteristics to conform to a desired range of properties. In one preferred method, referred to as the modified vapor diffusion process, the protein solution is placed in a second well near a first well. The first well is filled with a recipe solution and the second well is filled with a mixture of the protein solution and a smaller amount of the recipe solution than is present in the first well. A mixture of oils can be used to cover the first and/or second wells. The plate in which the first and second wells, respectively, or any number of first and second well pairs, are formed can be sealed with a clear cover or tape. Each well pair can be interconnected with a channel providing for vapor contact between each pair of first and second wells.

In one embodiment of the present method, a plate used in the invention having first and second wells, can include a plate that has a series of more than one set of first and second wells. In a particular aspect, the plate as described can be fabricated from a standard 384 well microplate where a channel between first and second wells in the same pair can be milled or otherwise formed by removal of a portion of the material between the adjacent wells such that the adjacent wells so connected by the channel are interconnected with one another when the plate is covered by a cover, by tape, or by other similar objects. Modulation of the degree of vapor communication between wells can be accomplished by variation in the size of the channel formed between each of the two interconnected wells. Variation in size of the channel can include variation in the depth, width or length of the channel. Alternatively, other devices or objects can be interposed in the functional channel between first and second wells of pairs. For example, a porous object, such as, but not limited to, a membrane or a sponge, can be interposed in the channel.

In another embodiment, recipe libraries can be prepared at much more dilute concentrations than those used by those skilled in the art. Similarly, protein solutions can be prepared at much more dilute concentrations. When either one, or both, of the solutions are prepared at more dilute concentrations, there are several benefits, including, but not limited to, more consistent and reliable dispensing of solutions. The greater accuracy and precision of solution dispensing steps occurs both during recipe preparation from the bulk solutions (which are now more diluted), and during preparation of the experiments in the low volume range. The excess water, relative to what is necessary to promote crystallization, can be removed by evaporation. The rate at which the excess water is removed by evaporation can be modified by adjusting the ratio of the water-permeable oils to the water-impermeable oils in the overlaying oil mixture, if the solution is overlayed with an oil or oil mixture. Alternatively, the droplet containing excess water can be covered initially with water-permeable oils that arrests the initial rapid evaporation following dispensing, but still provides for a reasonable loss of water over several days thereby allowing the concentrations of protein and ingredients to reach levels significant to the crystallization process. Optionally, once evaporation has proceeded to a point where the concentrations of protein and/or ingredients are significant to crystallization, an additional quantity of oil can be added to the well containing the droplet. The additional quantity of oil can be of the same composition and/or properties as the original oil used to overlay the droplet or it may differ. The use of the additional quantity of oil can be used to provide a slower evaporation rate such as is preferred for orderly crystal growth.

Alternatively, or in conjunction with an overlaying oil process, the rate of solvent evaporation can be altered by altering the humidity of the environment. In one aspect, the humidity of the environment can be increased to slow down the evaporation rate through the water permeable overlaying oil. In another aspect, the humidity of the environment can be decreased to increase the evaporation rate through the water permeable overlaying oil. Those skilled in the art can appreciate variations and combinations of the above embodiments to achieve the multiple objectives of control over the initial evaporation rate, control of the release of excess water in the solution, and control over the slow process kinetics at the latter stage of the experiment.

In another embodiment of the batch crystallization method provided by the invention, the protein solution is dispensed into a well adapted for crystallization prior to the recipe solution. The surface of the well can be adapted to modify its surface characteristics. While not being bound by theory, it is believed that the addition of protein solution to the well prior to addition of the recipe solution provides improved surface adhesion of the protein to the well's surface and a stable contact line between protein of the solution and the well surface. In contrast, when the recipe solution is dispensed first, the droplet formed from both the recipe solution and the protein solution does not adhere to the well surface as well and the resultant combined droplet is typically pushed to the wall junction of the well upon addition of the overlaying oil.

In another embodiment, the ratio of the protein solution to the recipe solution is varied across the crystallization array to provide an additional control variable during screening. The ratio of protein solution to recipe solution can be 1:99, 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, 95:5, 99:1, wherein x:y designates x volume protein solution and y volume recipe solution.

In another aspect, the invention provides a device or a series of devices used to prepare solutions for crystallization screens, to prepare recipe libraries for crystallization screens, and to conduct the crystallization screens themselves. By way of illustration, such devices are shown in FIGS. 1-6. The system illustrated in FIGS. 1-6 comprises two distinct devices. The first device, shown in FIG. 1 and referred to as RecipeMaker 10, is used to prepare recipe solutions from bulk solutions. The RecipeMaker can also re-format recipe solutions from their initial containers (e.g., 2 milliliter volume wells in 96 deep-well plates) into smaller containers (e.g., 80 microliter in 384 deep-well plates). This particular example of a RecipeMaker is based on a commercially available robotic liquid handler (the Microlab MPH-8, Hamilton Company, Reno, Nev.). In this example, the RecipeMaker 10 is outfitted with 8 dispensing tips that are movable via an XYZ directional arm 11 and 8 independently-controlled precision syringes, each having a volume of 500 milliliters. The arrangement of the component parts and functions of the RecipeMaker can be accomplished in many different ways, as known to those of skill in the art, so long as the arrangement achieves the functionality described herein.

In one embodiment of the present invention, therefore, the input valve for each syringe can be connected to a computer-controlled rotating distribution valve that is also connected to 8 different supply tubes that lead to bottles containing separate bulk solutions. This configuration, by providing access to 8 sets of 8 solutions, thus provides for access to 64 different bulk solutions. Those skilled in the art can appreciate that many other potential configurations can be constructed using different numbers of dispensing tips, syringes, distribution valves, and fluid delivery and transport means for accessing bulk solutions 12.

In another embodiment, the devices of the current invention are computer controlled and/or automated. A computer task file, containing the quantities desired from each solution used to form the recipes, can be read into the RecipeMaker control program. The program can then determine the bulk solutions to be connected via the distribution valves with the syringes, and thus to the dispensing tips to prepare the recipe. In a preferred control program for the apparatus, the control program rearranges the sequence of dispensing solutions in such a way as to minimize the cleaning cycles required. As a significant amount of time and bulk solution costs are associated with the need to flush and/or clean the fluidics passages when switching from one bulk solution to another, this construction provides a significant advantage over any protocol which does not program the controller so as to minimize the number of wash steps. For example, when preparing recipes from 18 different bulk solutions, each typically containing up to 6 different bulk solutions, the control program used for this embodiment of the invention manages to restrict the total number of system washes to 5 cycles and results in a significant savings in fluids and time.

Once the recipe solutions are prepared in the 1.5 milliliter plates, they can be sealed with commercially available heat seals (such as those available from Abgen, Inc., UK), bar-coded, and left to mix via liquid diffusion overnight. In alternative embodiments, the recipes can be mixed using other techniques known to those of skill in the art, such as, but not limited to, vortexing, shaking, and mechanical mixing using magnetic beads and an external magnetic source. Once mixed, the recipe solutions can be stored as recipe libraries for different periods of time as is suitable for the solutions and the format in which they are stored. For example, it is contemplated that the recipe libraries so formed can be stored in a manner analogous to combinatorial chemistry libraries that are used in the pharmaceutical industry for the discovery of new drugs. The RecipeMaker device, using a simple software command set available from the manufacturer, can also re-format a bulk recipe library from a first format, e.g., 96 well plates, into a second format, e.g., 384 well plates. The latter format can be re-sealed, and can be used for the source of recipe solutions in subsequent embodiments of the invention. For example, the 384 well plate can be used as the recipe solution source in the next device. It is thus clear to those skilled in the art that other robotic liquid handlers with different hardware configurations, different numbers of wells in the recipe plates, and different recipe storage arrangements can also be used.

The second device described herein for the purposes of illustrating certain aspects of the invention is shown in FIGS. 2-6, and is referred to as NanoScreen 20. This device comprises a fast solenoid liquid dispensing system. The fast solenoid dispensing system can be movable using an XYZ directional transport stage 21. The device may have a deck 22 upon which the recipe plate 23 (which can contain a multiplicity of recipe solutions), a protein plate 24 (which can contain a multiplicity of protein solutions) and a crystallization plate 25, also referred to as a nano plate 25 (which can be used to contain a multiplicity of crystal screening condition reactions), can be situated. The deck 22 can also comprise other components which can be used to perform ancillary operations including, but not limited to, quality control 26, calibration and washing stations 27.

Figure 2:
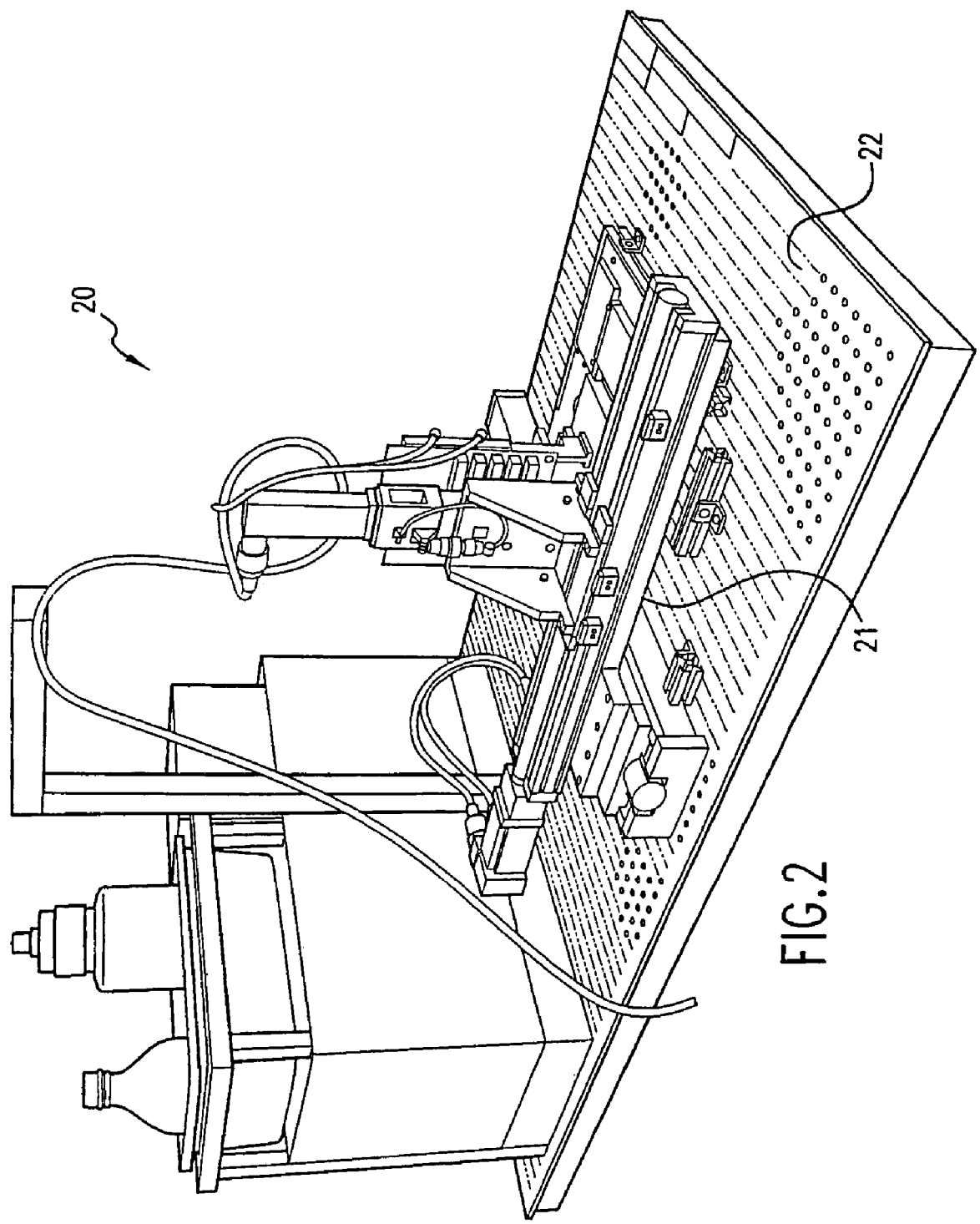
FIG. 2 is a depiction of the crystallization experiment preparation system, the NanoScreen device. The NanoScreen device is comprised of a computer controlled XYZ stage, a custom fast solenoid valve dispensing system and computer control software and computer control devices that direct action of the dispensing system.
Figure 4:
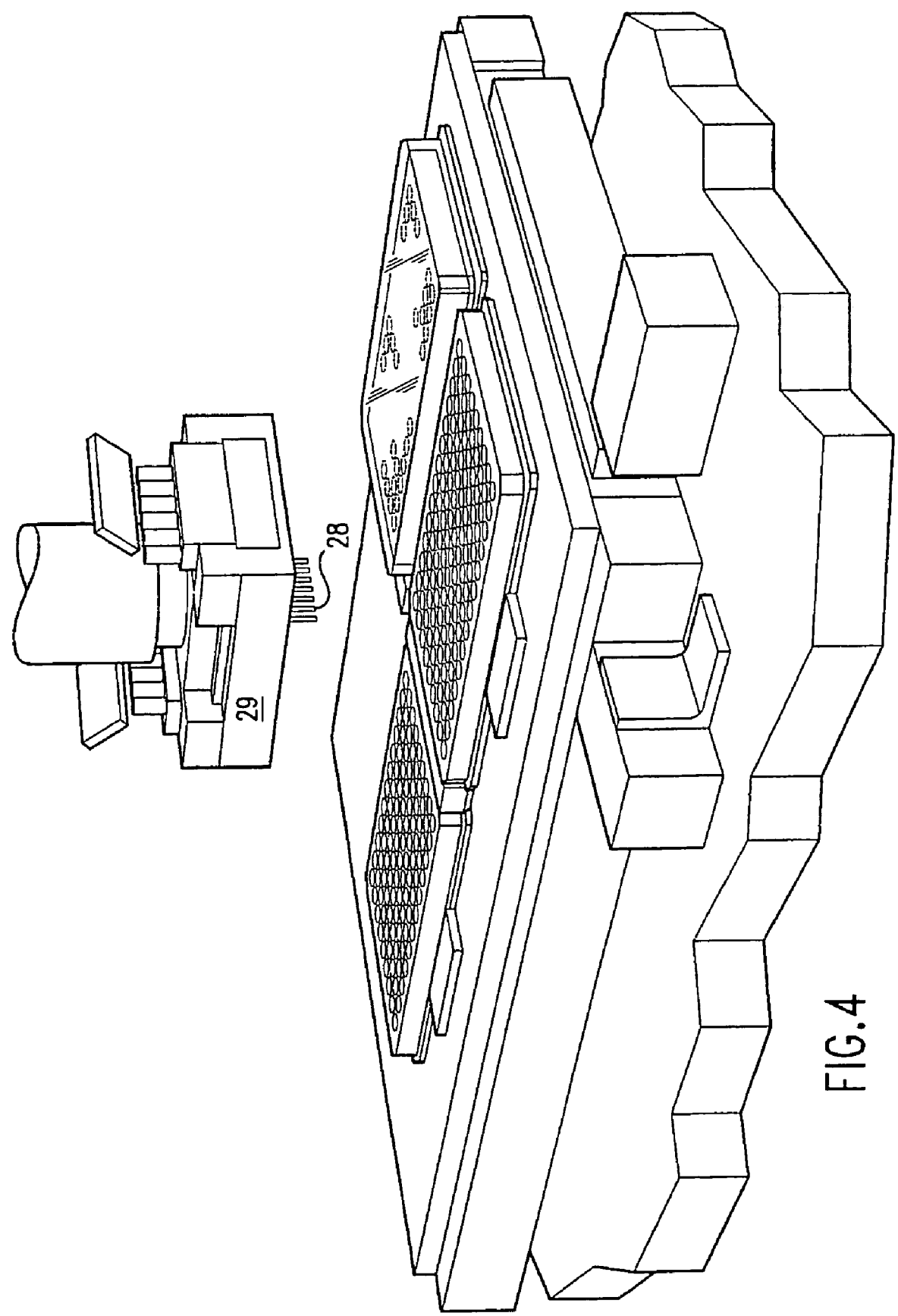
FIG. 4 is a depiction of the NanoScreen device showing the deck and dispense head. The close-up depiction clearly shows the dispensing tips array above the plates used in the practice of the invention.
Figure 5:
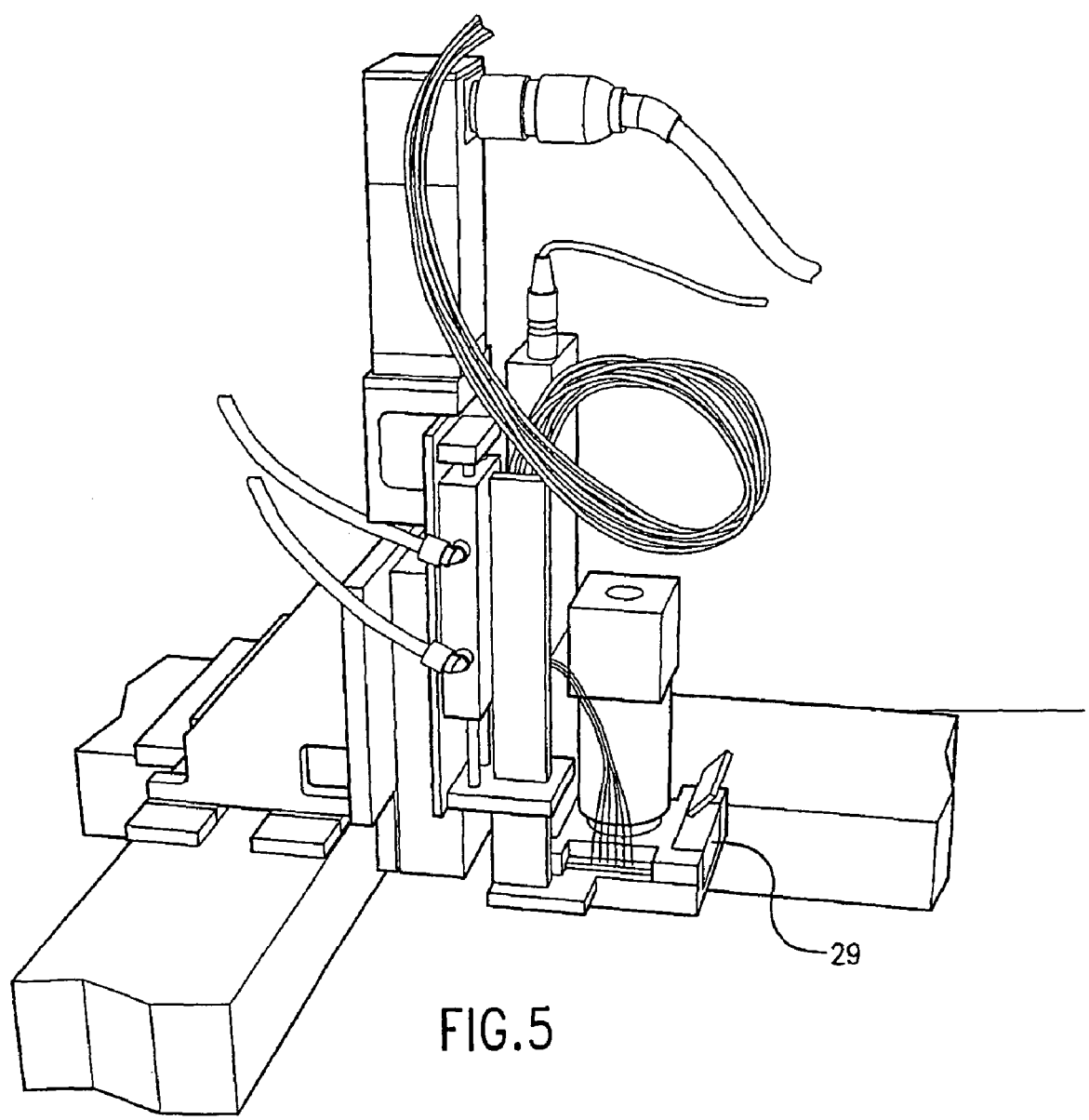
FIG. 5 is a depiction of the NanoScreen device showing the dispense head as mounted on the computer-controlled Z-axis stage.

NanoScreen's fast solenoid dispense system, shown in FIGS. 2, 4, and 5, combines commercially available components (Innovadyne, Inc., Santa Rose, Calif.), that include a fast switching valve, 12 fast solenoid valves, and 12 dispenser tips 28. Dispenser tips are mounted on a dispense head 29. The role of the fast switching valve is to rotate the fluidics passages for each tip between two positions. In the first position, each tip is fluidically connected to a computer-controlled syringe that is used to aspirate liquid solutions into the dispenser tip. The second position of the switching valve is use to connect each tip to a dedicated fast solenoid valve, that is further connected to a constant pressure supply. Further aspects of this fluidics subsystem include rotating valves providing the use of two syringes to aspirate liquids from 12 different solutions into 12 different tips, and a computer-controlled pressure regulator valve to provide precise pressure control at the desired level. A separate system dispenses oil using 12 flexible dispensing tips that are connected to fast solenoid valves (Lee, Inc. Westbrook, Conn.) and to a pressurized oil reservoir. The oil dispensing tips are mounted on an air cylinder providing a rapid motion in the Z-axis (vertically) between a top position used during motion of the entire dispense assembly, and a downward dispense position.

Figure 3:
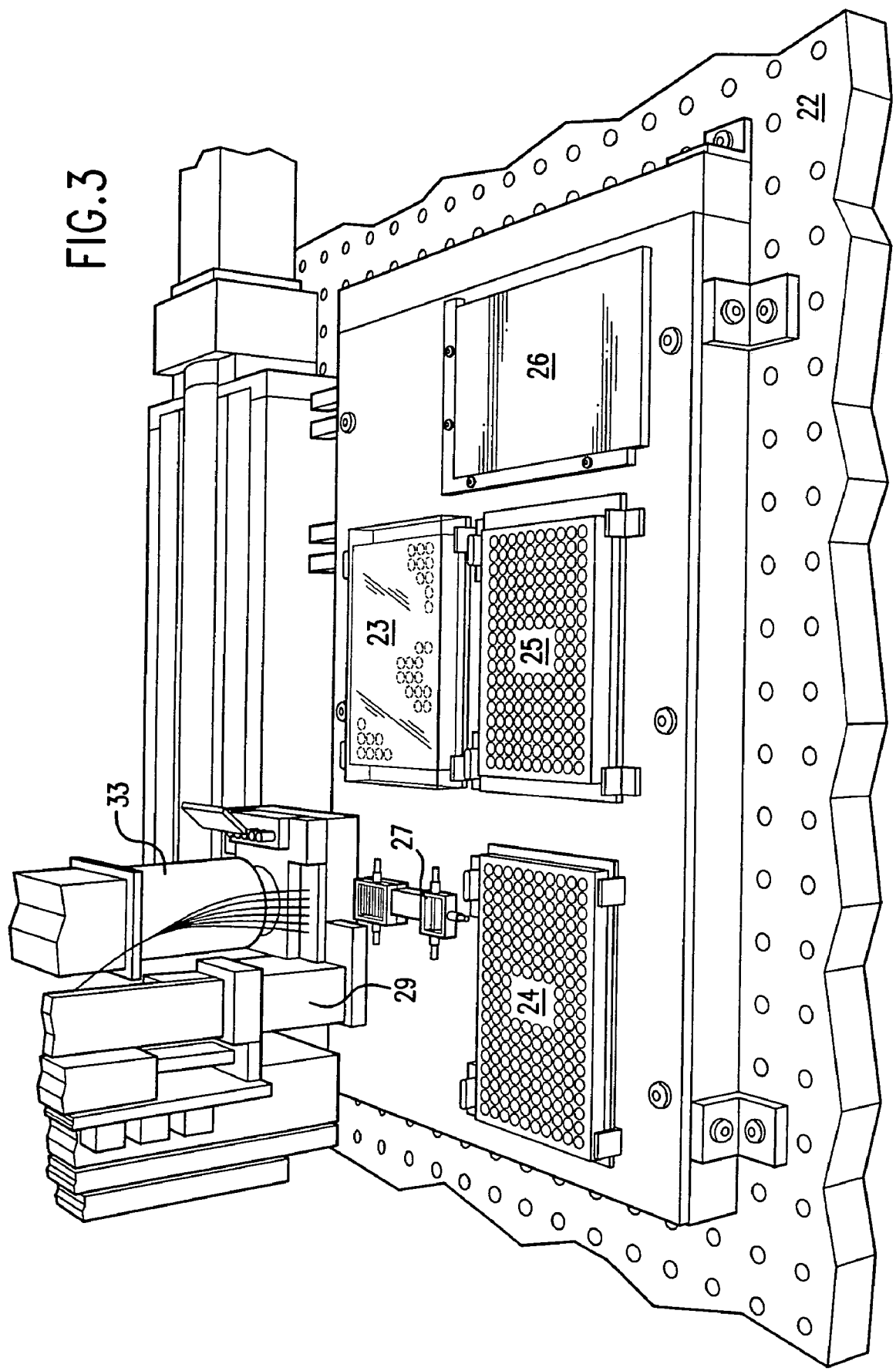
FIG. 3 is a depiction of the NanoScreen device showing the deck area. This close-up depiction of the deck area shows an exemplary arrangement of various plates, wash stations, and a quality control area of the device of the invention.

The deck area, shown in FIGS. 2 and 3, contains 3 holders for standard plate sizes: a recipe 384 well plate 23, a protein 384 well plate 24, and a crystallization 384 well plate 25. The recipe plate is a re-formatted 384 well plate that was prepared by RecipeMaker, the protein plate is a low-volume (40 microliter) 384 well plate, and the crystallization plate is a 384 well plate with a clear, flat bottom, and round wells. NanoScreen dedicates 2 of the 12 dispenser tips for dispensing the protein solutions. The protein plate thus contains protein solutions in only 2 of the wells, with other wells being used to return excess protein from the dispenser tips at the conclusion of the experiment run. It is also possible to use other plates, plate formats, or well configurations may be used. Many of these are commercially available and will be recognized as being suitable for use in the current invention by those of skill in the art.

The primary considerations for choosing a recipe plate is its long-term chemical compatibility, while the principal reason for choosing a protein plate is the low well volume. The crystallization plate should preferably have a clear well bottom to enable subsequent inspection for the appearance of crystals. Several additional plate formats specifically adapted for crystallization, and especially for vapor diffusion experiments with sitting drops, have recently become available (Corning, Inc., Acton, Mass., and Greiner Bio-One, Germany). While the plates used and described herein for the sake of illustration are chosen for their compatibility with the NanoScreen device, namely, the spacing (4.5 millimeter) for the NanoScreen dispenser tips, alternative plates can be used. Alternative dispenser tip spacings (e.g., 9 millimeter for 96 well plates) can be readily accommodated with the current design of the apparatus to provide for compatibility with other plates, such as the known types of commercial vapor diffusion plates (e.g., those supplied by Corning, Inc.).

Other components and sub-systems positioned or carried on the deck include an area or station designated for quality control 26. In the context of a small volume dispenser, quality control is comprised of a periodic verification that no dispenser tip in the dispenser tip array is clogged. The quality control area includes a removable glass surface, shown in FIG. 3, that is coated with a hydrophobic coating which results in a contact angle of approximately 90 degrees. A long range microscope equipped with a video camera is also provide, and is fixed to the dispenser head subsystem 29 and is thus movable with it using the same XYZ transport stage 21. The quality control station provides for the periodic dispensing of droplets from the dispenser tip array of desired liquid volumes on the glass surface, followed by automated machine vision inspection of these droplets.

Figure 6:
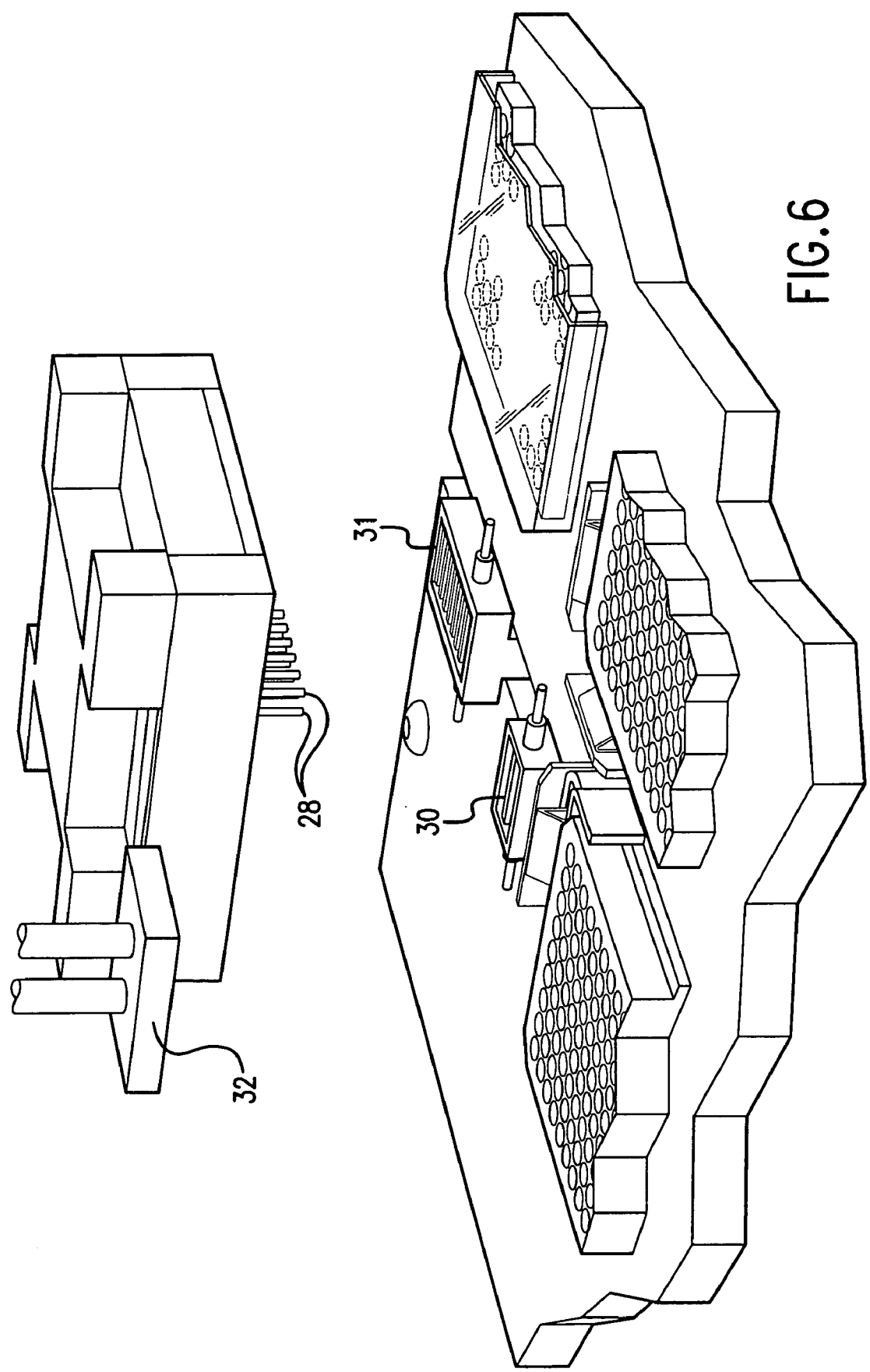
FIG. 6 is a depiction of certain aspects of the NanoScreen device adapted for cleaning the protein and recipe solution tips. This depiction illustrates features of the protein and recipe solution tip wash stations.

Yet another area on the deck, shown in FIG. 6, provides for the washing and drying of the dispenser tips. Since the NanoScreen device uses only two tips to dispense the protein solution, a wash station is provided for the protein tips 30. The wash station comprises a manifold into which the tips are lowered. A wash cycle is employed, in which the dispenser tips are externally saturated by strong jets of washing fluid, while simultaneously dispensing water through the tip and into the manifold. After a thorough cleaning of the tip's internal and external surfaces, a vacuum is provided to the manifold while the tips are kept in their inserted position to enable the rapid drying of the external surfaces. While the protein wash system has two holes in its manifold, the recipe wash system 31 has 10 such holes, with similar operations. The two wash systems provide for washing of the dispenser tips between aspirate/dispense cycles of the recipe solutions, and at the beginning and conclusion of the entire experiment for all of the dispenser tips 28.

The dispense, or dispenser, head system 29, together with the video camera (with the long range microscope) 33, is mounted on a commercially available XYZ directional transport stage (Parker-Hannifen, Cleveland, Ohio.), as shown in FIGS. 2 and 5. The XYZ transport stage has a 12 inch range of motion in the X and Y (planar) axes, and a 3 inch range of motion in the Z (vertical) axis. Movement along each access is accurate to within 25 micrometers (positional accuracy).

The NanoScreen device can be computer controlled. For example, the control program can be written in Visual Basic, C++ (Microsoft Corporation, Redmond, Wash.) and LabView (National Instruments, Austin, Tex.), that runs under the Windows 98 operating system (Microsoft Corporation, Redmond, Wash.). The control program can provide capabilities for deck calibration (positional determination of all fixtures relative to the XYZ stage), dispenser tip calibration, a set of service routines that include, e.g., manual stage control, fluidics priming, manual dispensing, etc., and assay parameters setup, including, e.g., volume and sequence of dispensing, length of time for tip washing, automated quality control cycles, and other functions as are described herein or are needed.

With the NanoScreen device, dispenser tip calibration can be performed by repeatedly dispensing water at several volume settings on the quality control surface, followed by machine vision determination of the actual volume dispensed for each setting using the video camera (with the long range microscope lens) 33. The control program then calculates a linear relationship between the volume setting and actual (measured) volumes, and stores the linear coefficients that are particular for each dispenser tip/valve fluidics system.

Each normal operation cycle is typically begun by priming the respective dispenser tip fluidics system and validating the integrity of each tip/valve fluidic system. This is normally accomplished by dispensing a desired volume on the quality control area 26. This can then be followed by automated image acquisition and display of each dispensed droplet to the operator or to a software system. The recipe 23, protein 24, and crystallization plates 25 are then loaded on the deck either manually or by a robotic operation. The cycle commences by the aspiration of protein solution from the protein wells into two dispenser tips. The tips are then moved to the quality control area and dispensing is performed, followed by machine vision inspection to determine the integrity of protein solution dispensing. Since protein solutions exhibit wide variations in their surface wetting, viscosity, and surface tension characteristics, it is important to verify that each particular protein solution could be adequately dispensed. If dispensing proves to be difficult, and the system returns the protein dispenser tips to the protein plate and dispenses the protein solution back into neighboring wells for later retrieval, dilution, or other processing steps. As provided in the assay setup parameters, the system performs a quality control cycle (dispensing followed by inspection) before commencing actual operations, periodically or as selected by the parameter settings.

Each cycle typically includes a recipe solution aspiration step, followed by protein solution dispense step, recipe solution dispense step, and the oil dispense step. The steps are performed in a block, defined as the number of dispenser tips in the recipe dispenser tip array (10 tips in the NanoScreen device depicted herein). The time required to dispense the protein and recipe solutions for each block is a few seconds, thus providing for the arrest of the fast evaporation thereof by immediate coverage of these solutions by the oil layer for each such block, the covering oil being provided by the controlled dispensing of oil from the oil manifold 32. The recipe solution tip array is then moved to the recipe solution wash station 31, and the recipe solution tips washed internally and externally. The cycle is then repeated for the number of blocks specified in the assay setup parameters. The remaining protein solution is returned to the protein plate 24, and the entire dispenser tip fluidics system is thereafter washed.

The NanoScreen and RecipeMaker devices/systems provide the means to perform the method of crystallization disclosed in the present invention. Improvements in the way the method of crystallization could be accomplished using modifications to or alternative devices/systems will be apparent to those skilled in the art.

EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

EXAMPLE 1

Figure 7:
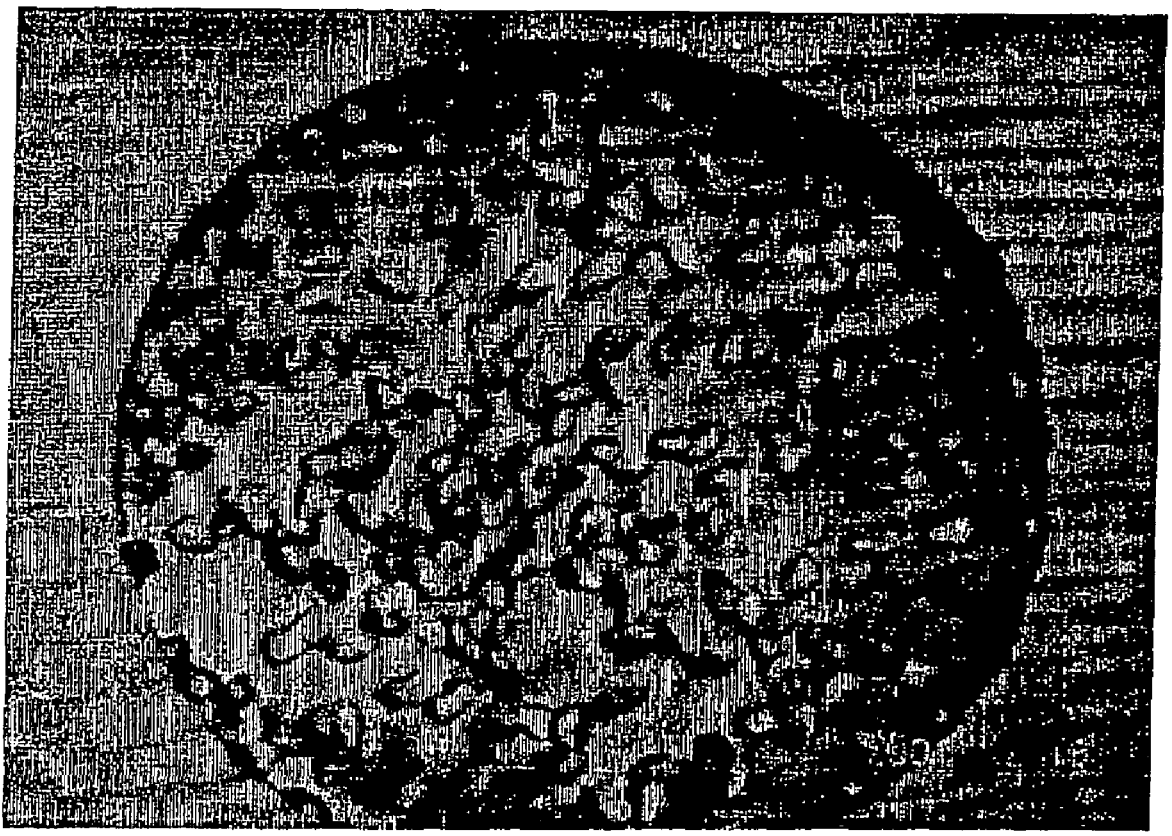
FIG. 7 depicts crystals of concanavalin-A protein formed in a droplet prepared by the RecipeMaker and NanoScreen devices. The droplet contained a total of 45 nanoliters of protein and recipe solution. Crystals appeared two days after preparation of the droplet after incubation at room temperature. Crystals were photographed using video microscopy.

Recipe solutions were prepared by the system shown in FIG. 1 using a statistical design of experiment methodology that combined ratios of ingredients from 18 types of bulk solutions. These solutions contained different buffers, salts, crystallization agents, and surfactants. The recipe solutions were prepared in 1.5 milliliter wells in 96 well plate and then sealed with tape. The ingredients were allowed to mix by diffusion over 24 hours, and then the recipe solutions were re-formatted into 384 plates. The recipe plates were placed on the deck of the dispenser shown in FIG. 7, a concanavalin-A protein solution was placed on another plate on the deck, and an empty crystallization screen plate containing 384 wells was also placed on the deck. The dispenser, having a plurality of tips for aspirating and dispensing of the protein and recipe solutions, automatically prepared an array of crystallization experiments. Each well contained a unique recipe and the same protein solution, and was immediately covered with a layer of 80/20% v/v paraffin to oil mixture. The dispensing volume of the protein solution was varied across the plate in three groups: 20, 40, and 60 nanoliter, and the recipe solutions volumes were also varied in three groups: 60, 40, and 20 nanoliter, such that the total droplet volume in each well was 80 nanoliter. The plates were then sealed with 3M Clear Tape and allowed to equilibrate at room temperature (about 21° C.). The wells were periodically examined using a video microscope system. A total of 450 wells were prepared in three 384 plates. Several of the wells showed growth of small crystals after a few days of incubation. FIG. 7 shows a typical well with crystals, where the droplet size was approximately 550 micrometers in diameter.

EXAMPLE 2

Figure 8:
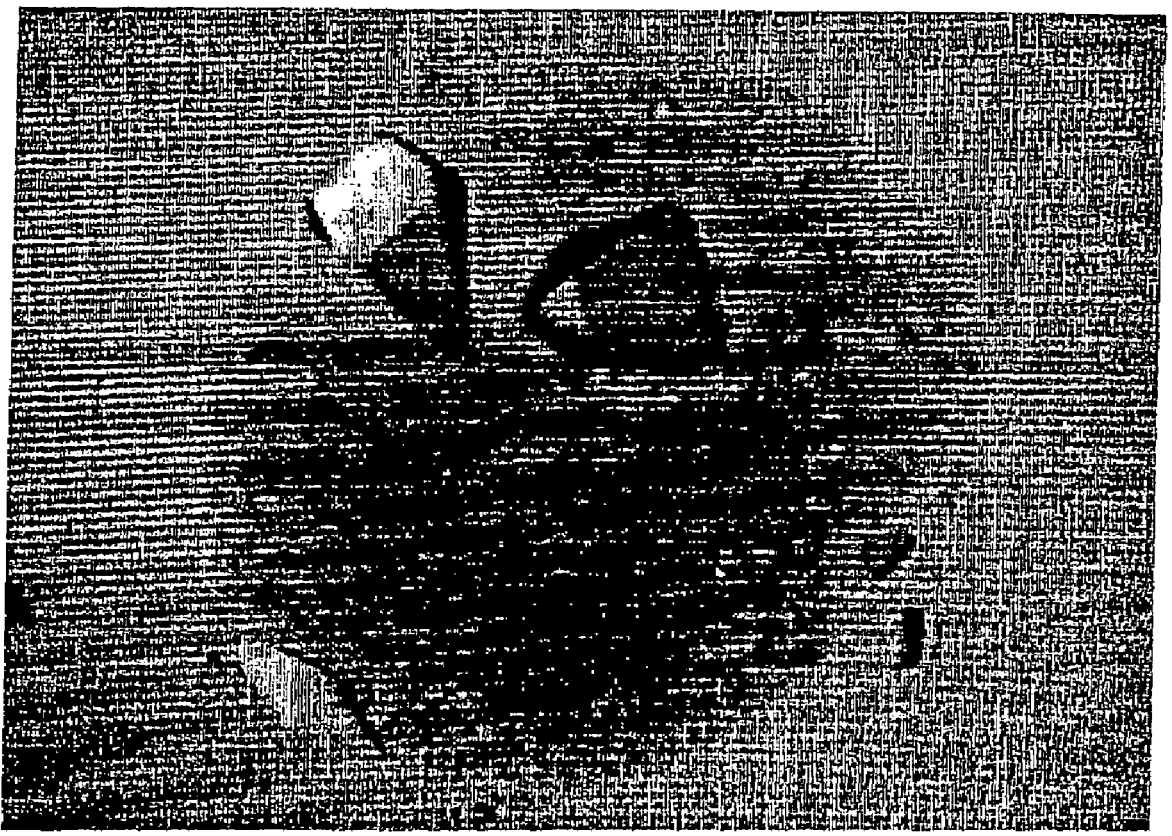
FIG. 8 depicts crystals of thaumatin protein formed in a droplet prepared by the RecipeMaker and NanoScreen devices. The droplet contained a total of 30 nanoliters of protein and recipe solution. Crystals appeared after approximately one day after preparation of droplet and incubation at room temperature. Crystals were photographed using video microscopy.
Figure 9:
FIG. 9 depicts crystals of thaumatin protein formed in a droplet prepared by the RecipeMaker and NanoScreen devices. The droplet contained a total of 45 nanoliters of protein and recipe solution. The crystals shown formed three days after preparation of the droplet and incubation at room temperature. Crystals were photographed using video microscopy.

An experiment using the same conditions, solutions, and apparatuses was repeated with thaumatin instead of concanavalin-A. Several wells produced very large crystals, as shown in FIGS. 8 and 9, where the droplet diameters were typically 500 micrometers.

EXAMPLE 3

A series of experiments using other proteins were conducted using the methods and devices of the present invention. The proteins listed in this example include both known and unknown proteins. The 2g1-1a and 9c9 proteins are unknown proteins from the NIH Structural Genomics project. 4g49a and peIAE are unknown proteins provided by other researchers. The act_2 protein is a chymotrypsinogen. The W539A protein is a chitinase from an unknown organism. The pf glutamate dehydrogenase is a bacterial protein.

Figure 10A:
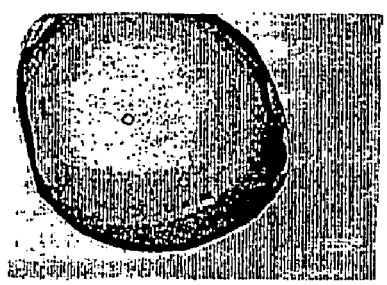
FIG. 10, parts A-O, depicts crystals of selected proteins formed in droplets prepared by use of the RecipeMaker and NanoScreen devices. Droplets depicted contained a total of 80 nanoliters of protein and recipe solution. The protein solution in each drop varied between 20 nanoliters and 51 nanoliters. The remainder volume necessary to bring the total volume to 80 nanoliters in each case was added solution containing buffer and precipitants.
Figure 10B:
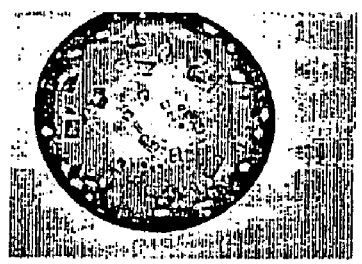
Figure 10C:
Figure 10D:
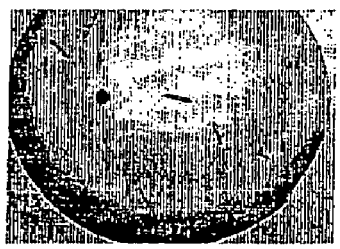
Figure 10E:
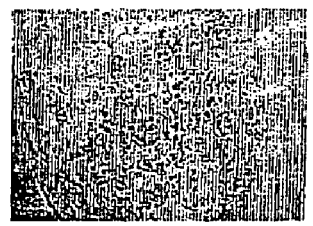
Figure 10F:
Figure 10G:
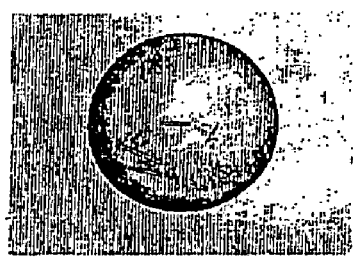
Figure 10H:
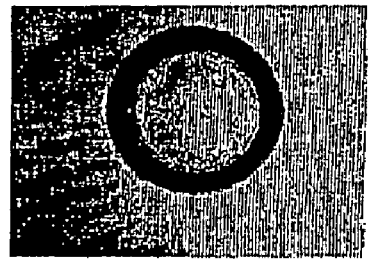
Figure 10I:
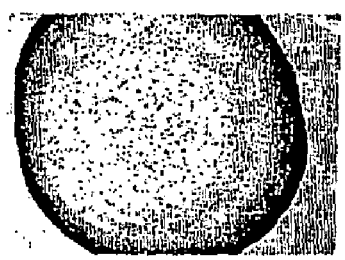
Figure 10J:
Figure 10K:
Figure 10L:
Figure 10M:
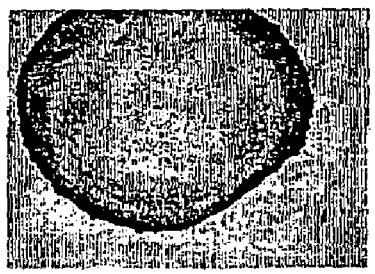
Figure 10N:
Figure 10O:
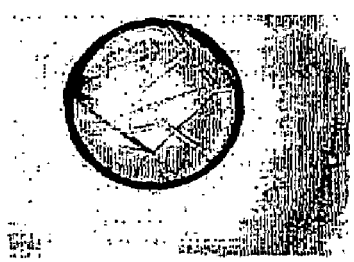

The results of these experiments, carried-out in accordance with the teachings of the present invention, can be seen in FIGS. 10A-O. In FIG. 10A, 2G1-1A was crystallized in 0.1 M Acetate (pH 4.5), 0.693 M NaCl, 12.37% PEGM5000, 0.01 M $CaCl_2$, and 0.05 M Arg-HCl at 4° C. In FIG. 10B, 2G1-1A was crystallized in 0.1 M Tris (pH 8.5), 0.2 M NaOAc, and 30% PEG4000 at 22° C. In FIG. 10C, 2g1-1a was crystallized in 0.1 M HEPES (pH 7.5), 0.289 M NaCl, 23.53% PEG4000, 6% glycerol, 0.01 M $MgCl_2$ and 0.05% BOG at 4° C. In FIG. 10D, 4g49a was crystallized in 0.1 M HEPES (pH 7.5) and 1.5 M $LiSO_4$ at 22° C. In FIG. 10E, 9c9 was crystallized in 0.1 M HEPES (pH 7.5), 0.264 sodium malonate, 4.7% PEG8000, 3% glycerol, 0.01 M $MgCl_2$ and 0.05 M ArgHCl at 4° C. In FIG. 10F, 9c9 was crystallized in 0.1 M Bicine (pH 9), 0.11 M sodium citrate, 8.85% PEGM5000, 6% glycerol, 0.01 M $CaCl_2$, and 0.05 M ArgHCl at 14° C. In FIG. 10G, act_2 was crystallized in 0.1 M Bicine (pH 8.3), 0.264 M ammonium sulfate$_4$, 4.79% PEG4000, 6% glycerol, 0.01 M $MgCl_2$ at 22° C. In FIG. 10H, pelAE was crystallized in 0.1 M Bicine (pH 9), 0.479 M sodium citrate, 9.49% MPD, 0.01 M $MgCl_2$, and 0.05 M ArgHCl at 22° C. In FIG. 10I, glutamate dehydrogenase was crystallized in 0.1 M HEPES (pH 7.5) and 4.3 M NaCl at 22° C. In FIG. 10J, glutamate dehydrogenase was crystallized in 0.1 M MES (pH 6), 0.599 M sodium acetate, 10.65% PEG8000, and 0.05% BOG at 22° C. In FIG. 10K, arsenate reductase was crystallized in 0.1 M Bicine (pH 8.3), 0.16 M ammonium sulfate, 14.3% MPD, 6% glycerol, 0.01 M $MgCl_2$, and 0.05 M ArgHCl at 14° C. In FIG. 10L, arsenate reductase was crystallized in 0.1 M MES (pH 6), 0.25 M sodium malonate, and 20.06% PEGM5000 at 22° C. In FIG. 10M, W539A was crystallized in 0.1 M HEPES (pH 7.5), 0.289 M KSCN, 23.1% PEG8000 and 0.05% BOG at 4° C. In FIG. 10N, W539A was crystallized in 0.1 M HEPES (pH 7.5), 0.25 M NaCl, 19.97% PEG8000, 3% glycerol and 0.05 M ArgHCl at 14° C. In FIG. 10O, 9c9 was crystallized in 0.1 M MES (pH 6), 0.2 M sodium malonate, 16.26% PEG4000, 3% glycerol, and 0.01% $CaCl_2$ at 14° C.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A crystallization experiment preparation system, comprising:
   a) dispense head provided with plurality of fluid dispenser tips;
   b) a video camera and a long range microscope each carried on said dispense head;
   c) a stage constructed and arranged to move the dispense head, the video camera, and the long range microscope together in the X, the Y, and the Z directions;
   d) a deck area positioned with respect to the stage, said deck area having at least one fixture for receiving at least one recipe plate, at least one protein plate, at least one crystallization plate, a quality control area, and a wash system thereon.

2. A crystallization experiment preparation system, comprising:
   a) a dispense head provided with plurality of fluid dispenser tips;
   b) a video camera and a long range microscope each carried on said dispense head;
   c) a deck area positioned with respect to the dispense head, said deck area having at least one fixture for receiving at least one recipe plate, at least one protein plate, at least one crystallization plate, a quality control area, and a wash system thereon;
   d) wherein the dispense head, the video camera, and the long range microscope are held together in a stationary position with respect to a deck area; and
   e) wherein the deck area is constructed and arranged to be moved with respect to the dispense head, the video camera, and the long range microscope by a stage movable in the X, the Y, and the Z, directions.

3. A crystallization experiment preparation system, comprising:
   a) a dispense head provided with plurality of fluid dispenser tips;
   b) a video camera and a long range microscope each carried on said dispense head;
   c) a first stage on which the dispense head is positioned, said first stage being constructed and arranged to move the dispense head in the Z direction;
   d) a deck area positioned with respect to the dispense head, said deck area having at least one fixture for receiving at least one recipe plate, at least one protein plate, at least one crystallization plate, a quality control area, and a wash system thereon; and
   e) a second stage adapted to carry said deck area in the X and the Y directions.

4. The crystallization experiment preparation system of claim 3, said dispense head further comprising an aspiration and dispensing system.

5. The crystallization experiment preparation system of claim 4, said aspiration and dispensing system comprising a constant pressure fast solenoid.

6. The crystallization experiment preparation system of claim 4, said aspiration and dispensing system comprising a piezo device.

7. The crystallization experiment preparation system of claim 4, said aspiration and dispensing system comprising a syringe-driven fast solenoid.

8. The crystallization experiment preparation system of claim 3, further comprising a dispenser tip fluidics system, said dispenser tip fluidics system comprising a plurality of fluid dispenser tips.

9. The crystallization experiment preparation system of claim 8, wherein each dispenser tip of the tip fluidics system is individually calibrated.

10. The crystallization experiment preparation system of claim 9, wherein each said individually calibrated dispenser tips has an individual calibration curve used to dispense a measured and predetermined volume of a protein solution or a recipe solution there through.

11. The crystallization experiment preparation system of claim 3, further comprising at least one droplet array, each said at least one droplet array comprising at least one protein solution and at least one recipe solution prepared in blocks of protein and recipe solutions.

12. The crystallization experiment preparation system of claim 11, wherein the total time required to prepare each said protein solution and recipe solution block ranges from about one to about sixty seconds.

13. A method for screening protein crystal growth conditions comprising the steps of:
 a) providing a crystallization experiment preparation system comprising a dispense head provided with plurality of fluid dispenser tips; a video camera and a long range microscope each carried on said dispense head; a first stage on which the dispense head is positioned, said first stage being constructed and arranged to move the dispense head in the Z direction; a deck area positioned with respect to the dispense head, said deck area having at least one fixture for receiving at least one recipe well plate, at least one protein well plate, at least one crystallization well plate, a quality control area, and a wash system thereon; and a second stage adapted to carry said deck area in the X and the Y directions;
 b) dispensing a volume of protein solution containing a protein into at least one of the wells;
 c) dispensing a recipe solution into at least one of the wells, wherein the recipe solutions was prepared from bulk ingredients prior to being dispensed into the wells and was stored in a plurality of containers or in a second multiwell plate;
 d) subjecting the protein solution, or a combination solution formed by the combination of the protein solution with the recipe solution, to environmental conditions effective to form protein crystals; and
 e) detecting protein crystal growth.

\* \* \* \* \*